(12) United States Patent
Naseri et al.

(10) Patent No.: US 12,064,360 B2
(45) Date of Patent: Aug. 20, 2024

(54) PROSTHETIC FOOT

(71) Applicants: Amirreza Naseri, Shiraz (IR); Majid Mohammadi Moghaddam, Tehran (IR); Maziar Ahmad Sharbafi, Darmstadt (DE); Mohammad Gharini, Tehran (IR)

(72) Inventors: Amirreza Naseri, Shiraz (IR); Majid Mohammadi Moghaddam, Tehran (IR); Maziar Ahmad Sharbafi, Darmstadt (DE); Mohammad Gharini, Tehran (IR)

(73) Assignee: Tarbiat Modares University, Tehran (IR)

( * ) Notice: Subject to any disclaimer, the term of this patent is extended or adjusted under 35 U.S.C. 154(b) by 45 days.

(21) Appl. No.: 17/092,356

(22) Filed: Nov. 9, 2020

(65) Prior Publication Data

US 2021/0106441 A1 Apr. 15, 2021

Related U.S. Application Data

(60) Provisional application No. 62/933,376, filed on Nov. 9, 2019.

(51) Int. Cl.
*A61F 2/66* (2006.01)
*A61F 2/68* (2006.01)
(Continued)

(52) U.S. Cl.
CPC .............. *A61F 2/6607* (2013.01); *A61F 2/68* (2013.01); *A61F 2002/5072* (2013.01);
(Continued)

(58) Field of Classification Search
CPC .. A61F 2/6607; A61F 2/68; A61F 2/74; A61F 2/748; A61F 2002/5072; A61F 2002/6657
See application file for complete search history.

(56) References Cited

U.S. PATENT DOCUMENTS

2012/0130508 A1* 5/2012 Harris ...................... A61F 2/68
623/50
2014/0088730 A1* 3/2014 Hansen ................ A61F 2/6607
623/52
(Continued)

OTHER PUBLICATIONS

Kikuchi, Takayuki, et al. "Non-Energized Above Knee Prosthesis Enabling Stairs Ascending and Descending with Hydraulic Flow Controller." Journal of Robotics and Mechatronics 30.6 (2018): 892-899. (Year: 2018).*

*Primary Examiner* — Jerrah Edwards
*Assistant Examiner* — Maximilian Tobias Spencer
(74) *Attorney, Agent, or Firm* — Bajwa IP Law Firm; Haris Zaheer Bajwa

(57) ABSTRACT

A passive ankle-foot prosthesis to replicate a human foot. The passive ankle-foot prosthesis includes a foot part, an ankle frame, a yoke, and a spring. The ankle frame is attached fixedly to a second end of the foot part. The yoke is configured to be attached to a residual limb of a user. A first end of the yoke is pivotally attached to a first end of the ankle frame utilizing a pivot. The yoke is configured to rotate around a pivot axis. The pivot axis passes through the pivot. The spring is disposed between the ankle frame and the yoke. A first end of the spring is connected to a second end of the yoke. A second end of the spring is connected to a second end of the ankle frame. The spring is configured to apply an upward force to the second end of the ankle frame based on the yoke's rotational movements.

11 Claims, 19 Drawing Sheets

(51) Int. Cl.
*A61F 2/74* (2006.01)
*A61F 2/50* (2006.01)
(52) U.S. Cl.
CPC ......... *A61F 2002/6657* (2013.01); *A61F 2/74* (2021.08); *A61F 2/748* (2021.08)

(56) References Cited

U.S. PATENT DOCUMENTS

2014/0222167 A1* 8/2014 Poulson, III .......... A61F 2/6607
623/52
2015/0305895 A1* 10/2015 Boiten ..................... A61F 2/66
623/26

* cited by examiner

424

PROSTHETIC FOOT

CROSS-REFERENCE TO RELATED APPLICATION

This application claims the benefit of priority from U.S. Provisional Patent Application Ser. No. 62/933,376, filed on Nov. 9, 2019, and entitled "HYBRID HYDRAULIC ANKLE PROSTHETIC FOOT" which is incorporated herein by reference in its entirety.

TECHNICAL FIELD

The present disclosure generally relates to prostheses, and particularly, to prosthetic feet and, more particularly, to a passive prosthetic foot that is able to replicate a human foot at a specific activity level.

BACKGROUND

Human locomotion, such as walking and running, is commonly described in terms of gait. Gait may be defined as a cyclical or reoccurring pattern of a leg and/or a foot movement, rotation, and torques that may create human locomotion. Due to the repetitive nature of gait, gait may be typically analyzed in terms of percentages of a gait cycle. A gait cycle may be defined for a single leg beginning with an initial contact of a foot with a surface such as the ground. An initial contact of a foot on the ground may be referred to as a heel strike where a foot's heel may first be in contact with the ground. The conclusion of a gait cycle may occur when the same foot makes the next heel strike. A gait cycle may be divided into two phases: a stance phase and a swing phase. The stance phase may refer to a part of a gait cycle where a foot is in contact with a surface such as the ground. The swing phase may begin when a foot is in the air and, consequently, not in contact with the ground. The swing phase may begin when a foot leaves contact with the ground and may end with a heel strike of the same foot.

Prosthetic and orthotic devices can help restore mobility to people who lack able-bodied motion or gait. Prosthetic devices are intended to replace a function and/or an appearance of a missing limb and can return mobility to a wearer or user. Orthotic devices are intended to support or supplement an existing limb, by assisting with movement, reducing weight-bearing loads on a human body, reducing pain, and controlling or restricting movement. Prosthetic and orthotic devices may be available to replace or support various portions of a human body. Lower limb prosthetic devices include, for example, prosthetic foot, foot-ankle prosthesis, prosthetic knee joint, and prosthetic hip joint. Lower limb orthotic devices include, for example, the foot orthoses, the ankle-foot orthoses, the knee-ankle-foot orthoses, and the knee orthoses. People who require a lower limb prosthesis or orthosis often expend more metabolic power to walk or move at the same speed as able-bodied individuals. One goal of lower limb prosthetic and orthotic devices is to help a user in achieving a normal gait while reducing energy expended by the user.

The gait dynamics of a human joint can be described in terms of the position, velocity, moment, and power. During a typical walking gait cycle, the moment required from a human ankle reaches a maximum value of approximately 1.25 Newton meters per kilogram of body weight, while the typical rotational velocity of the human ankle may reach a maximum of approximately 215 degrees per second, and the maximum power consumed by the human may reach approximately 3.5 Watts per kilogram of body weight. One goal of prosthetic and orthotic devices is to match characteristics of able-bodied gait of an equivalent physiological structure.

Prosthetic and orthotic devices are generally divided into three groups: passive devices, active devices, and bionic devices. Passive lower limb prosthetics generally rely on compliant members, such as springs, to store and release energy. A spring may be able to only return as much energy as is put into the spring, minus efficiency losses. Thus, an energy that is released by a spring may be limited to an energy that is put into the spring by a user. Additionally, existing spring-based prosthetic ankles return the energy insufficiently and lack sufficient power return to produce a normal gait for a user. A user of a prosthetic ankle may expend additional energy through recruiting other muscles and joints in a compensation strategy to maintain a functional gait. Therefore, passive prosthetic devices may be limited in capacity to reduce a user's metabolic energy expenditure while achieving a normal walking gait and performing other activities. Some studies have shown a 10-30% increase in metabolic cost for walking over able-bodied norms, depending on amputation level and gait speed.

Furthermore, prosthetic devices are designed to perform more similarly to a human muscle during a variety of activities. Compliant prosthetic devices are typically designed for a specific activity, such as walking. The majority of compliant devices utilize a traditional rigid structure. An activity-specific design strategy and traditional rigid structures may be suited for one specific activity, but the designs are limited in application and are not efficient beyond the intended activity. For example, devices designed for walking perform poorly for running, navigating uneven terrain, walking up and down inclines or stairs, or simply balancing while standing. Carrying heavy loads or transitioning from walking to running remains a challenge for users. There is, therefore, a need for a prosthetic foot that is able to reduce a user's metabolic energy expenditure while achieving a normal walking gait and performing other activities. Furthermore, there is a need for a prosthetic foot that is able to perform well and satisfactorily for various tasks associated with a human foot such as walking, running, navigating uneven terrain, walking up and down inclines or stairs, or simply balancing while standing.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to one or more exemplary embodiments of the present disclosure, a passive ankle-foot prosthesis is disclosed. In an exemplary embodiment, the passive ankle-foot prosthesis may include a foot part, an ankle frame, a yoke, and a spring. In an exemplary embodiment, a value of the spring constant may be in a range between 35 N/mm$^2$ and 50 N/mm$^2$. In an exemplary embodiment, the foot part may include a bottom deflectable base plate and a top deflectable plate. In an exemplary embodiment, a first end of the top deflectable plate may be attached to the bottom deflectable base plate. In an exemplary embodiment, a second end of the top deflectable plate may be configured to deflect relative to the first end of the top deflectable plate.

In an exemplary embodiment, the ankle frame may be attached fixedly to the second end of the top deflectable plate. In an exemplary embodiment, the yoke may be configured to be attached to a residual limb of a user. In an exemplary embodiment, a first end of the yoke may be pivotally attached to a first end of the ankle frame utilizing a pivot. In an exemplary embodiment, the yoke may be configured to rotate around a pivot axis. In an exemplary embodiment, the pivot axis may pass through the pivot.

In an exemplary embodiment, the spring may be disposed between the ankle frame and the yoke. In an exemplary embodiment, a first end of the spring may be connected to a second end of the yoke. In an exemplary embodiment, a second end of the spring may be connected to a second end of the ankle frame. In an exemplary embodiment, the spring may be configured to apply an upward force to the second end of the ankle frame based on the yoke's rotational movements. In an exemplary embodiment, the spring may be configured to stretch when the yoke rotates in a clockwise direction around the pivot axis.

In an exemplary embodiment, the passive ankle-foot prosthesis may further include a hydraulic mechanism interconnected between the ankle frame and the yoke. In an exemplary embodiment, the hydraulic mechanism may be configured to resist against rotational movement of the yoke around the pivot axis.

In an exemplary embodiment, the hydraulic mechanism may further include a hydraulic cylinder and a hydraulic piston. In an exemplary embodiment, the hydraulic cylinder may be filled with a hydraulic oil. In an exemplary embodiment, the hydraulic cylinder may be fixedly attached to the yoke. In an exemplary embodiment, a first end of the hydraulic piston may be disposed slidably inside the hydraulic cylinder. In an exemplary embodiment, a second end of the hydraulic piston may be connected to the ankle frame. In an exemplary embodiment, the hydraulic piston may include a disc slider at the second end of the hydraulic piston. In an exemplary embodiment, the disc slider may be disposed movably inside the guide elongated hole. In an exemplary embodiment, the disc slider may include a disc shape.

In an exemplary embodiment, the hydraulic cylinder may include a top hydraulic chamber above the hydraulic piston and a bottom hydraulic chamber under the hydraulic piston. In an exemplary embodiment, the bottom hydraulic chamber may be in fluid communication with the top hydraulic chamber.

In an exemplary embodiment, the passive ankle-foot prosthesis may further include a guide elongated hole on the ankle frame. In an exemplary embodiment, the second end of the hydraulic piston may be disposed movably inside the guide elongated hole. In an exemplary embodiment, the guide elongated hole may be configured to control movements of the hydraulic piston inside the hydraulic cylinder.

In an exemplary embodiment, the guide elongated hole may include a first curved surface, a second curved surface, and a third curved surface. In an exemplary embodiment, a first end of the second curved surface may be connected to a second end of the first curved surface. In an exemplary embodiment, the second curved surface may include an arc of a circle. In an exemplary embodiment, a center of the circle may pass through the pivot axis. In an exemplary embodiment, a first end of the third curved surface may be connected to a second end of the second curved surface. In an exemplary embodiment, a second end of the third curved surface may be connected to a first end of the first curved surface.

In an exemplary embodiment, the guide elongated hole may be configured to urge the hydraulic piston to move inside the hydraulic cylinder and in a first direction due to the second end of the hydraulic piston moving along the first curved surface from the second end of the first curved surface to the first end of the first curved surface when the yoke rotates in the counter-clockwise direction from a first position to a second position. In an exemplary embodiment, the first position may be associated with a first point of the user's gait cycle. In an exemplary embodiment, the second position may be associated with a second point of the user's gait cycle.

In an exemplary embodiment, the guide elongated hole may be configured to urge the hydraulic piston to move inside the hydraulic cylinder and in a second direction due to the second end of the hydraulic piston moving along the first curved surface from the first end of the first curved surface to the second end of the first curved surface when the yoke rotates in the clockwise direction from the second position to a third position. In an exemplary embodiment, the third position may be associated with a third point of the user's gait cycle.

In an exemplary embodiment, the guide elongated hole may be configured to prevent movement of the hydraulic piston inside the hydraulic cylinder due to the second end of the hydraulic piston moving along the second curved surface from the first end of the second curved surface to the second end of the second curved surface when the yoke rotates in the clockwise direction from the third position to a fourth position. In an exemplary embodiment, it may be understood that the circular formation of the second curved surface may prevent the hydraulic piston movements inside the hydraulic cylinder when the yoke rotates in the clockwise direction from the third position to the fourth position. In an exemplary embodiment, a length and a shape of the first curved surface and a length and a shape of the second curved surface may be configured in such a way that the range of motion may never exceed the predicted path of the first curved surface and the second curved surface. In an exemplary embodiment, the fourth position may be associated with a fourth point of the user's gait cycle.

In an exemplary embodiment, the guide elongated hole may be configured to prevent movement of the hydraulic piston inside the hydraulic cylinder due to the second end of the hydraulic piston moving along the second curved surface from the second end of the second curved surface to the first end of the second curved surface when the yoke rotates in the counter-clockwise direction from the fourth position to a fifth position. In an exemplary embodiment, it may be understood that the circular formation of the second curved surface may prevent the hydraulic piston movements inside the hydraulic cylinder when the yoke rotates in the counter-clockwise direction from the fourth position to the fifth position. In an exemplary embodiment, the fifth position may be associated with a fifth point of the user's gait cycle.

In an exemplary embodiment, the spring may be configured to apply no force to the yoke and to the ankle frame due to the spring being disengaged from the ankle frame when the yoke rotates in the counter-clockwise direction from the first position to the second position. In an exemplary embodiment, the spring may be configured to apply no force to the yoke and to the ankle frame due to the spring being disengaged from the ankle frame when the yoke rotates in the clockwise direction from the second position to the third position.

In an exemplary embodiment, the spring may be configured to stretch when the yoke rotates in the clockwise direction from the third position to the fourth position. In an exemplary embodiment, the spring may be configured to apply an upward force to the ankle frame and apply a downward force to the yoke due to the spring being stretched when the yoke rotates in the counter-clockwise direction from the fourth position to the fifth position In an exemplary embodiment, the hydraulic mechanism may further include a hydraulic circuit configured to control fluid communication between the top hydraulic chamber and the bottom hydraulic chamber. In an exemplary embodiment, the hydraulic circuit may include a first hydraulic hose with a first check valve and a first regulating valve. In an exemplary embodiment, the hydraulic circuit may further include a second hydraulic hose with a second check valve and a second regulating valve.

In an exemplary embodiment, the top hydraulic chamber and the bottom hydraulic chamber may be in fluid communication through the first hydraulic hose. In an exemplary embodiment, the first check valve may be configured to allow fluid communication from the top hydraulic chamber to the bottom hydraulic chamber through the first hydraulic hose. In an exemplary embodiment, the first check valve may further be configured to prevent fluid communication from the bottom hydraulic chamber to the top hydraulic chamber through the first hydraulic hose. In an exemplary embodiment, the first regulating valve may be configured to control fluid flow from the top hydraulic chamber to the bottom hydraulic chamber through the first hydraulic hose.

In an exemplary embodiment, the top hydraulic chamber and the bottom hydraulic chamber may be in fluid communication through the second hydraulic hose. In an exemplary embodiment, the second check valve may be configured to allow fluid communication from the bottom hydraulic chamber to the top hydraulic chamber through the second hydraulic hose. In an exemplary embodiment, the second check valve may further be configured to prevent fluid communication from the top hydraulic chamber to the bottom hydraulic chamber through the second hydraulic hose. In an exemplary embodiment, the second regulating valve may be configured to control fluid flow from the bottom hydraulic chamber to the top hydraulic chamber.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed a passive ankle-foot prosthesis. An exemplary passive ankle-foot prosthesis may include a foot part, an ankle frame attached to the foot part, a yoke configured to be attached to a residual limb of an amputee, a spring disposed between the ankle frame and the yoke, and a hydraulic mechanism including a hydraulic cylinder and a hydraulic piston. The hydraulic cylinder may be attached to the yoke. A first end of the hydraulic piston may be disposed slidably inside the hydraulic cylinder. A second end of the hydraulic piston may be attached to the ankle frame. The spring may apply an upward force to the ankle frame. The hydraulic mechanism may act as a damper for movements of the yoke relative to the ankle frame. In other words, the hydraulic mechanism may resist against movements of the yoke relative to the ankle frame. When the hydraulic mechanism resists against movements of the yoke relative to the ankle frame, the yoke may move more slowly. The spring and the hydraulic mechanism in an exemplary passive ankle-foot prosthesis may help an amputee to walk more comfortably by providing a push-off power and removing the breaking effect.

Figure 1A:
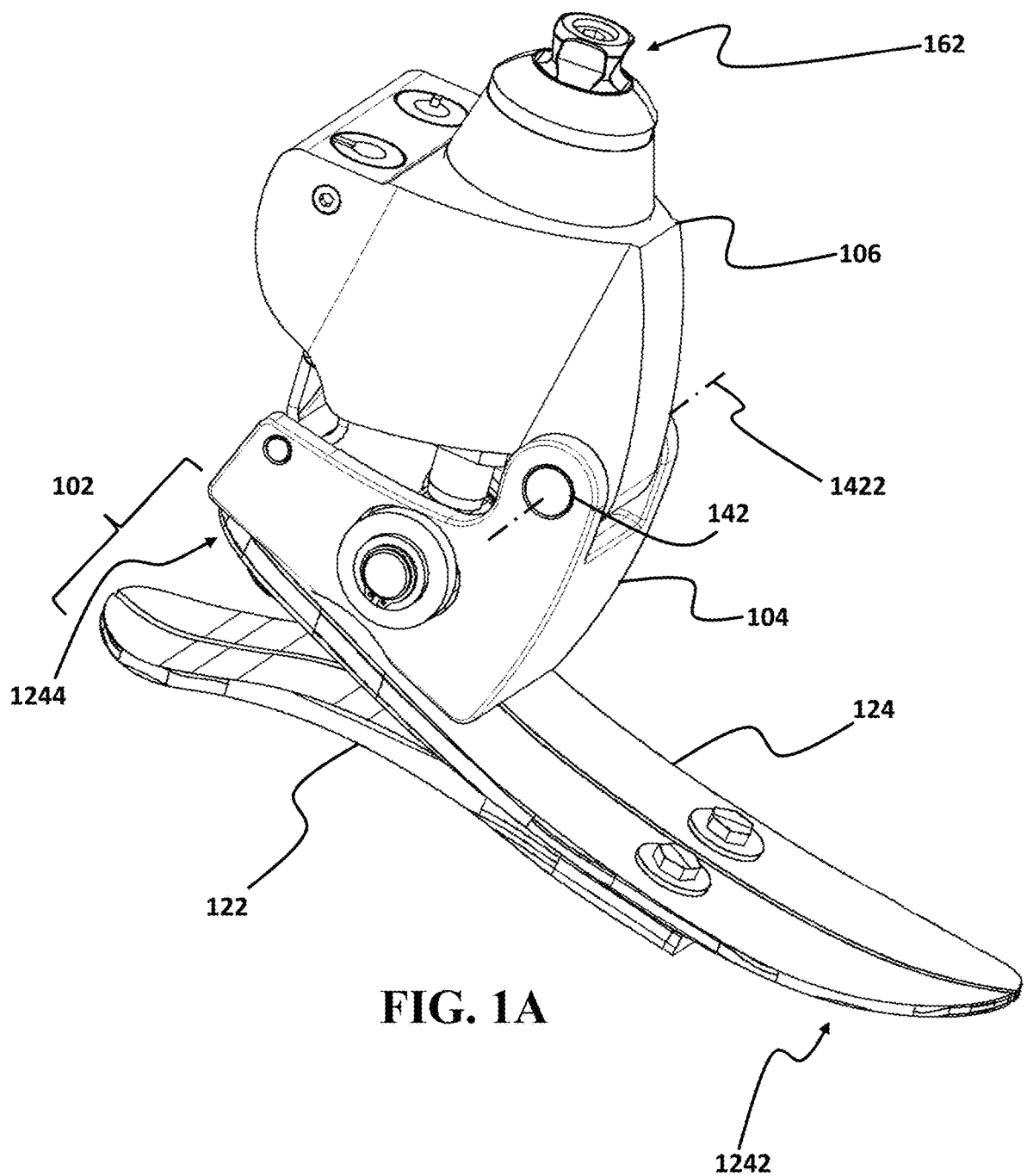
FIG. 1A illustrates a perspective view of a passive ankle-foot prosthesis, consistent with one or more exemplary embodiments of the present disclosure.
Figure 1B:
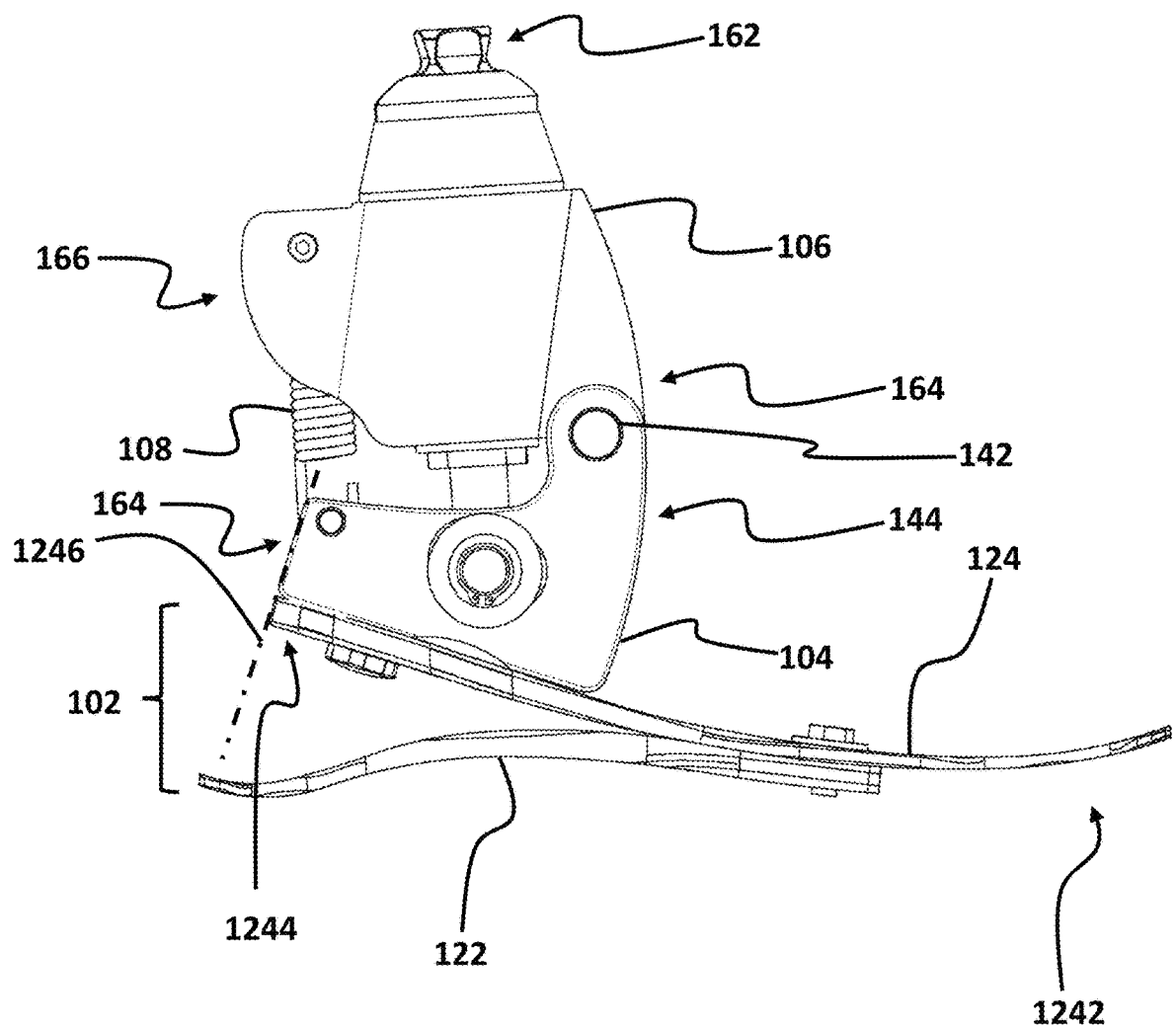
FIG. 1B illustrates a side view of a passive ankle-foot prosthesis, consistent with one or more exemplary embodiments of the present disclosure.
Figure 1C:
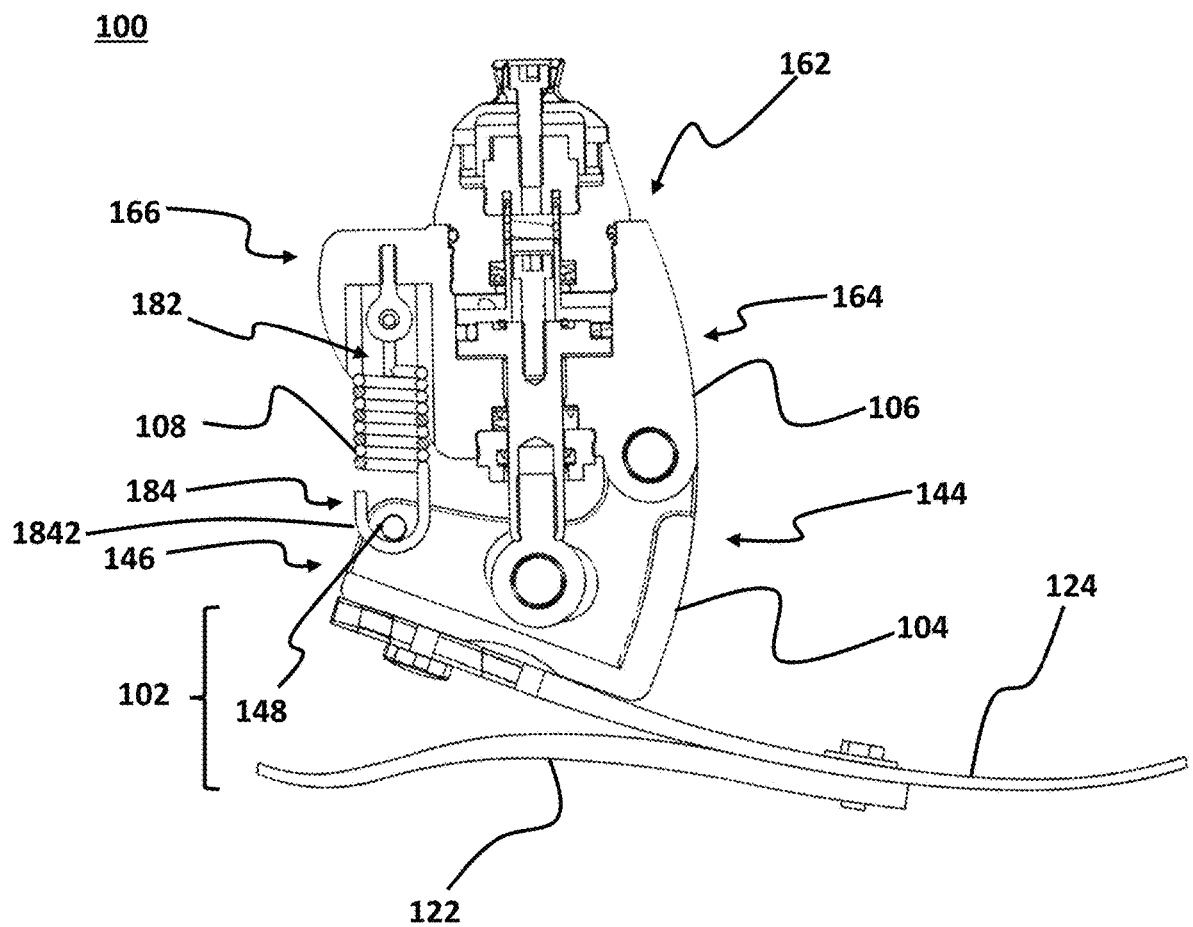
FIG. 1C illustrates a section side view of a passive ankle-foot prosthesis, consistent with one or more exemplary embodiments of the present disclosure.
Figure 1D:
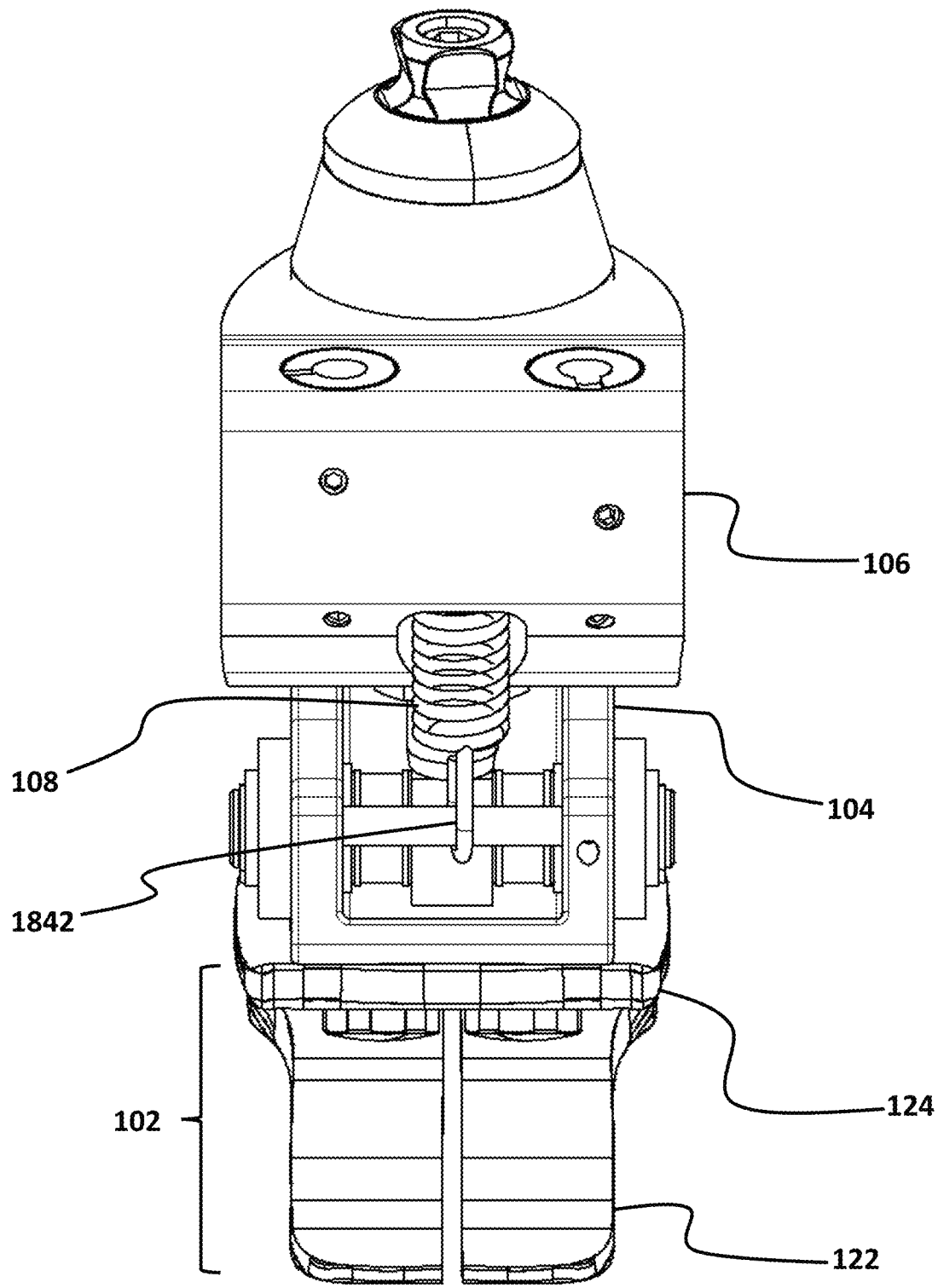
FIG. 1D illustrates a back view of a passive ankle-foot prosthesis, consistent with one or more exemplary embodiments of the present disclosure.
Figure 1E:
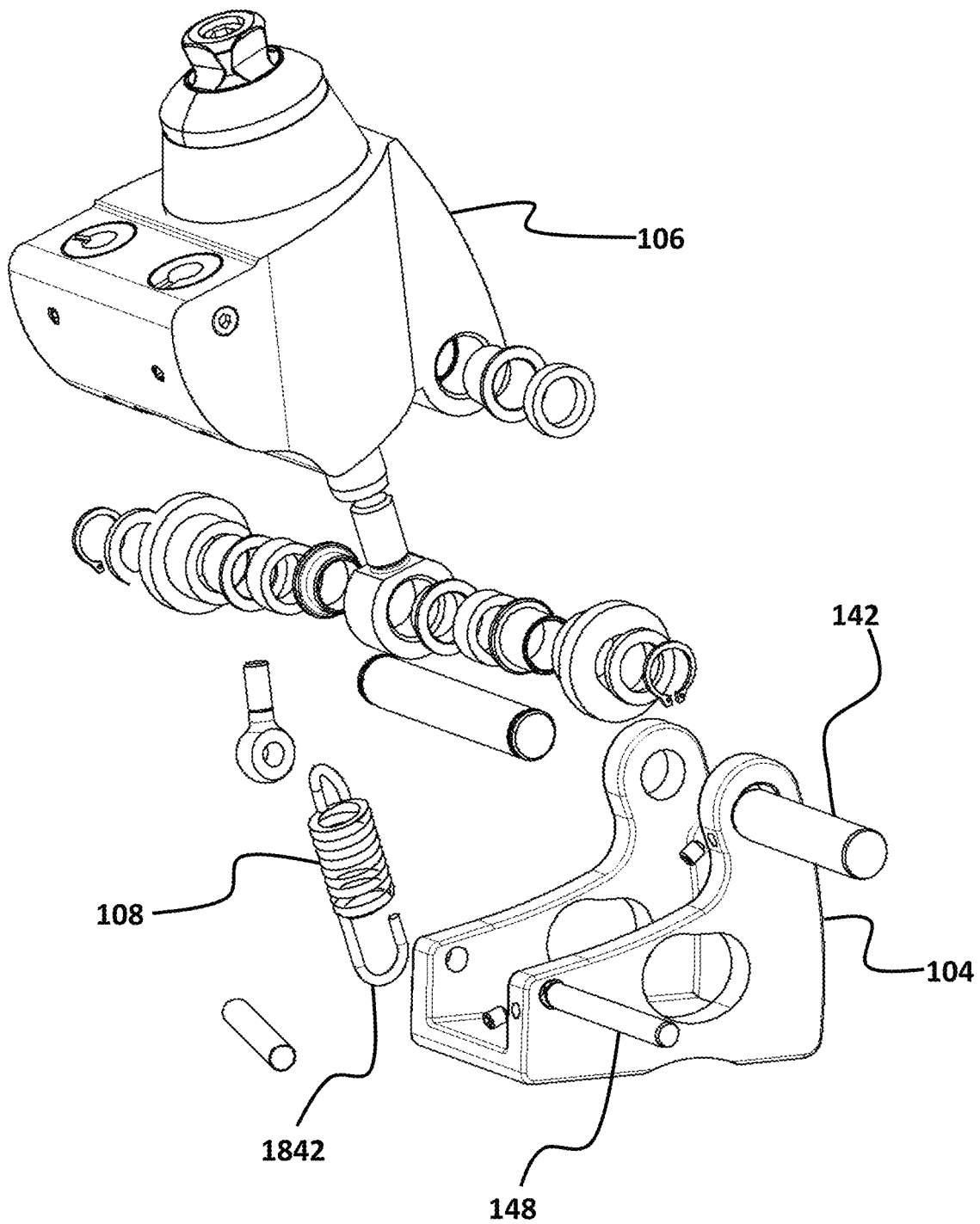
FIG. 1E illustrates an exploded view of a passive ankle-foot prosthesis, consistent with one or more exemplary embodiments of the present disclosure.
Figure 2:
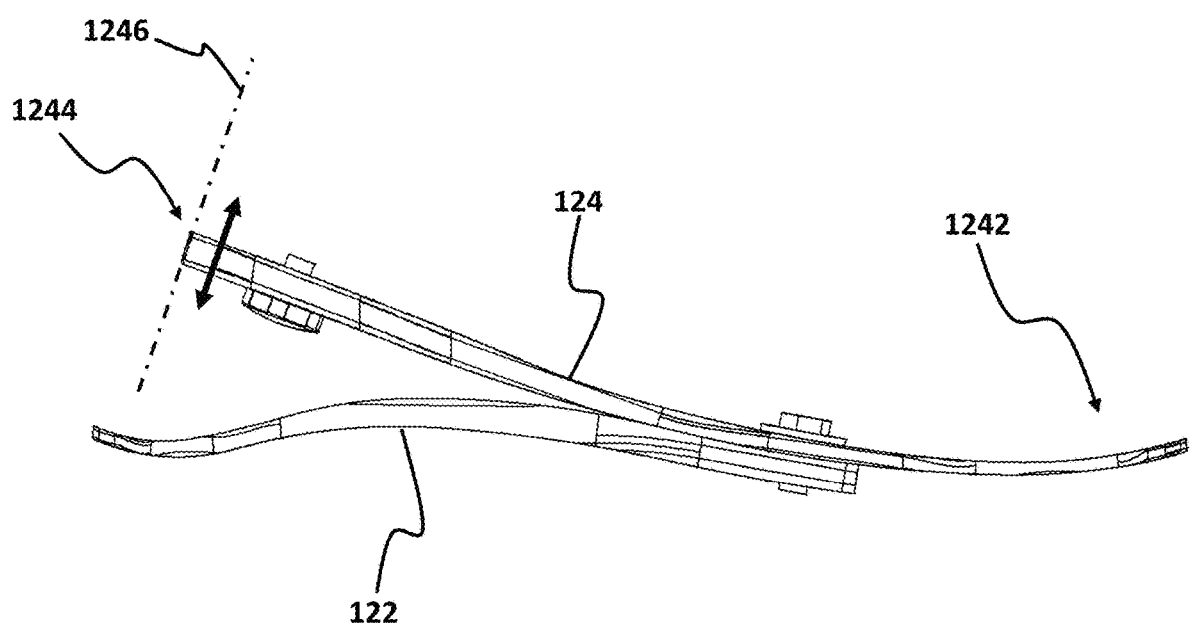
FIG. 2 illustrates a side view of a foot part, consistent with one or more exemplary embodiments of the present disclosure.

FIG. 1A shows a perspective view of a passive ankle-foot prosthesis 100, consistent with one or more exemplary embodiments of the present disclosure. FIG. 1B shows a side view of passive ankle-foot prosthesis 100, consistent with one or more exemplary embodiments of the present disclosure. FIG. 1C shows a section side view of passive ankle-foot prosthesis 100, consistent with one or more exemplary embodiments of the present disclosure. FIG. 1D shows a back view of passive ankle-foot prosthesis 100, consistent with one or more exemplary embodiments of the present disclosure. FIG. 1E shows an exploded view of passive ankle-foot prosthesis 100, consistent with one or more exemplary embodiments of the present disclosure. As shown in FIG. 1A, FIG. 1B, FIG. 1C, and FIG. 1D, in an exemplary embodiment, passive ankle-foot prosthesis 100 may include a foot part 102, an ankle frame 104, a yoke 106, and a spring 108. FIG. 2 shows a side view of foot part 102, consistent with one or more exemplary embodiments of the present disclosure. As shown in FIG. 2, in an exemplary embodiment, foot part 102 may include a bottom deflectable base plate 122 and a top deflectable plate 124. In an exemplary embodiment, bottom deflectable base plate 122 may be configured to be placed onto a surface. For example, when an amputee walks on a surface, bottom deflectable base plate 122 may be in contact with the surface. In an exemplary embodiment, the surface may be either a flat surface or an inclined surface. In an exemplary embodiment, a first end 1242 of top deflectable plate 124 may be attached to bottom deflectable base plate 122. In an exemplary embodiment, a second end 1244 of top deflectable plate 124 may be configured to deflect relative to first end 1242 of top deflectable plate 124. In an exemplary embodiment, when a user performs a gait cycle, a force may be applied to second end 1244 of top deflectable plate 124, and thereby, second end 1244 of top deflectable plate 124 may deflect relative to first end 1242 of top deflectable plate 124. In an exemplary embodiment, deflection of second end 1244 of top deflectable plate 124 relative to first end 1242 of top deflectable plate 124 may refer to a movement of second end 1244 of top deflectable plate 124 relative to first end 1242 of top deflectable plate 124 along a deflection axis 1246. In an exemplary embodiment, deflection axis 1246 may be an axis that is perpendicular to a main plain of deflectable plate 124.

In an exemplary embodiment, ankle frame 104 may be attached fixedly to second end 1244 of top deflectable plate 124. In an exemplary embodiment, it may be understood that when ankle frame 104 is attached fixedly to second end 1244 of top deflectable plate 124, ankle frame 104 may be attached to second end 1244 of top deflectable plate 124 in such a way that any movement between ankle frame 104 and second end 1244 of top deflectable plate 124 may be prevented or minimized.

In an exemplary embodiment, a top end 162 of yoke 106 may be configured to be attached to a residual limb of a user. In an exemplary embodiment, it may be understood that the user may refer to an amputee with an amputated leg. In an exemplary embodiment, the residual limb may refer to an amputated leg of an amputee. In an exemplary embodiment, a first end 164 of yoke 106 may be pivotally attached to a first end 144 of ankle frame 104 utilizing a pivot 142. In an exemplary embodiment, it may be understood that when first end 164 of yoke 106 is pivotally attached to first end 144 of ankle frame 104, yoke 106 may be able to rotate around a pivot axis 1422. In an exemplary embodiment, pivot axis 1422 may pass through pivot 142.

In an exemplary embodiment, spring 108 may be disposed between ankle frame 104 and yoke 106. In an exemplary embodiment, a first end 182 of spring 108 may be connected to a second end 166 of yoke 106. In an exemplary embodiment, a second end 184 of spring 108 may be connected to a second end 146 of ankle frame 104. In an exemplary embodiment, second end 184 of spring 108 may include a hook 1842. In an exemplary embodiment, ankle frame 104 may include a hook receiving rod 148 at second end 146 of ankle frame 104. In an exemplary embodiment, hook receiving rod 148 may be configured to be engaged with hook 1842. In an exemplary embodiment, it may be understood that when a length of spring 108 is larger than a natural length of spring 108, spring 108 may stretch and, to thereby, apply a downward force to second end 166 of yoke 106. Furthermore, when a length of spring 108 is larger than a natural length of spring 108, spring 108 may apply an upward force to second end 146 of ankle frame 104. In an exemplary embodiment, it may be understood that when a length of spring 108 is larger than a natural length of spring 108, spring 108 may pull ankle frame 104 up by applying an upward force to second end 146 of ankle frame 104.

Figure 3A:
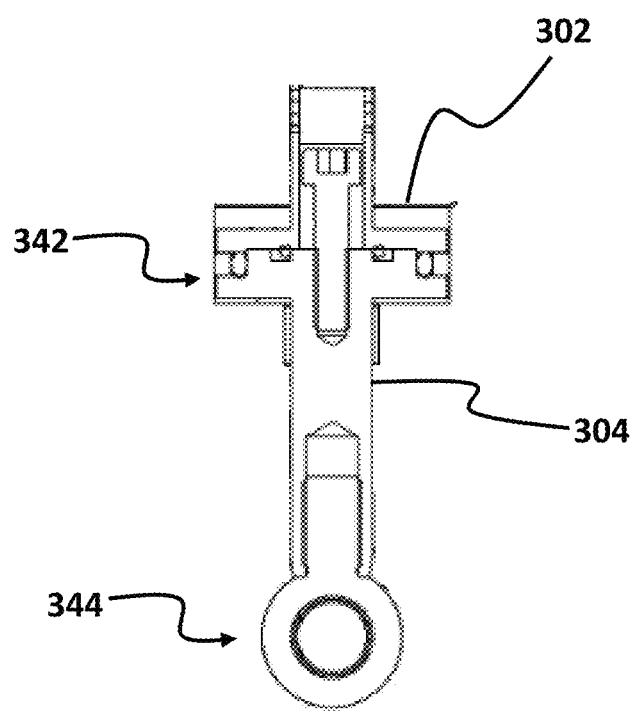
FIG. 3A illustrates a side view of a hydraulic mechanism, consistent with one or more exemplary embodiments of the present disclosure.

As shown in FIG. 1C, in an exemplary embodiment, passive ankle-foot prosthesis 100 may further include a hydraulic mechanism 105. In an exemplary embodiment, hydraulic mechanism 105 may be interconnected between ankle frame 104 and yoke 106. In an exemplary embodiment, hydraulic mechanism 105 may be configured to resist against rotational movement of yoke 106 around pivot axis 1422. FIG. 3A shows a side view of hydraulic mechanism 105, consistent with one or more exemplary embodiments of the present disclosure. As shown in FIG. 3A, in an exemplary embodiment, hydraulic mechanism 105 may include a hydraulic cylinder 302 and a hydraulic piston 304. In an exemplary embodiment, a first end 342 of hydraulic piston 304 may be disposed slidably inside hydraulic cylinder 302.

In an exemplary embodiment, hydraulic cylinder 302 may be filled with a hydraulic oil. As shown in FIG. 1C, in an exemplary embodiment, hydraulic cylinder 302 may be fixedly attached to yoke 106. In an exemplary embodiment, it may be understood that when hydraulic cylinder 302 is fixedly attached to yoke 106, hydraulic cylinder 302 is attached to yoke 106 in such a way that any movement between hydraulic cylinder 302 and yoke 106 may be prevented. In an exemplary embodiment, a second end 344 of hydraulic piston 304 may be connected to ankle frame 104.

Figure 3B:
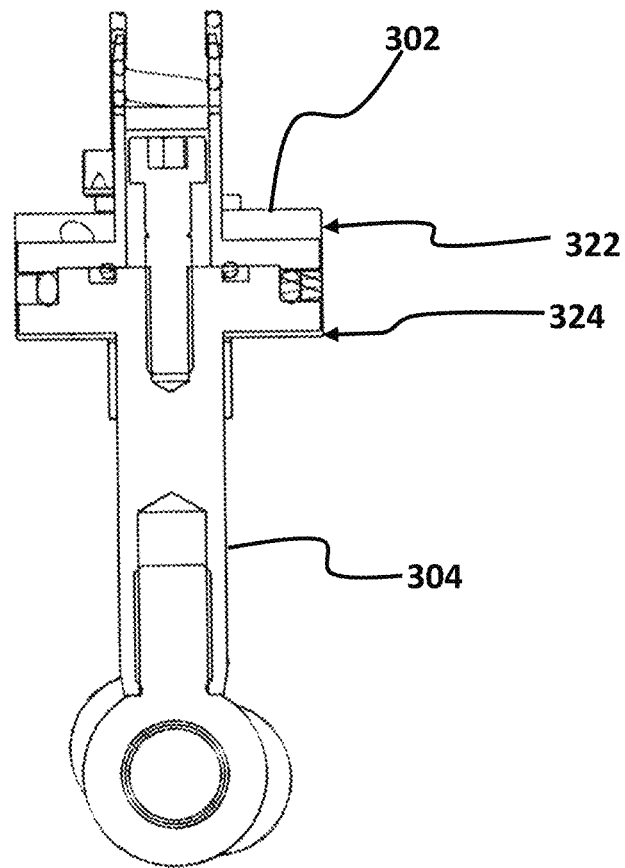
FIG. 3B illustrates another side view of a hydraulic mechanism, consistent with one or more exemplary embodiments of the present disclosure.

FIG. 3B shows another side view of hydraulic mechanism 105, consistent with one or more exemplary embodiments of the present disclosure. As shown in FIG. 3B, in an exemplary embodiment, hydraulic cylinder 302 may include a top hydraulic chamber 322 and a bottom hydraulic chamber 324. In an exemplary embodiment, top hydraulic chamber 322 may refer to a section of hydraulic cylinder 302 which may be present above hydraulic piston 304. In an exemplary embodiment, bottom hydraulic chamber 324 may refer to a section of hydraulic cylinder 302 which may be present under hydraulic piston 304. In an exemplary embodiment, bottom hydraulic chamber 324 may be in fluid communication with top hydraulic chamber 322.

Figure 4A:
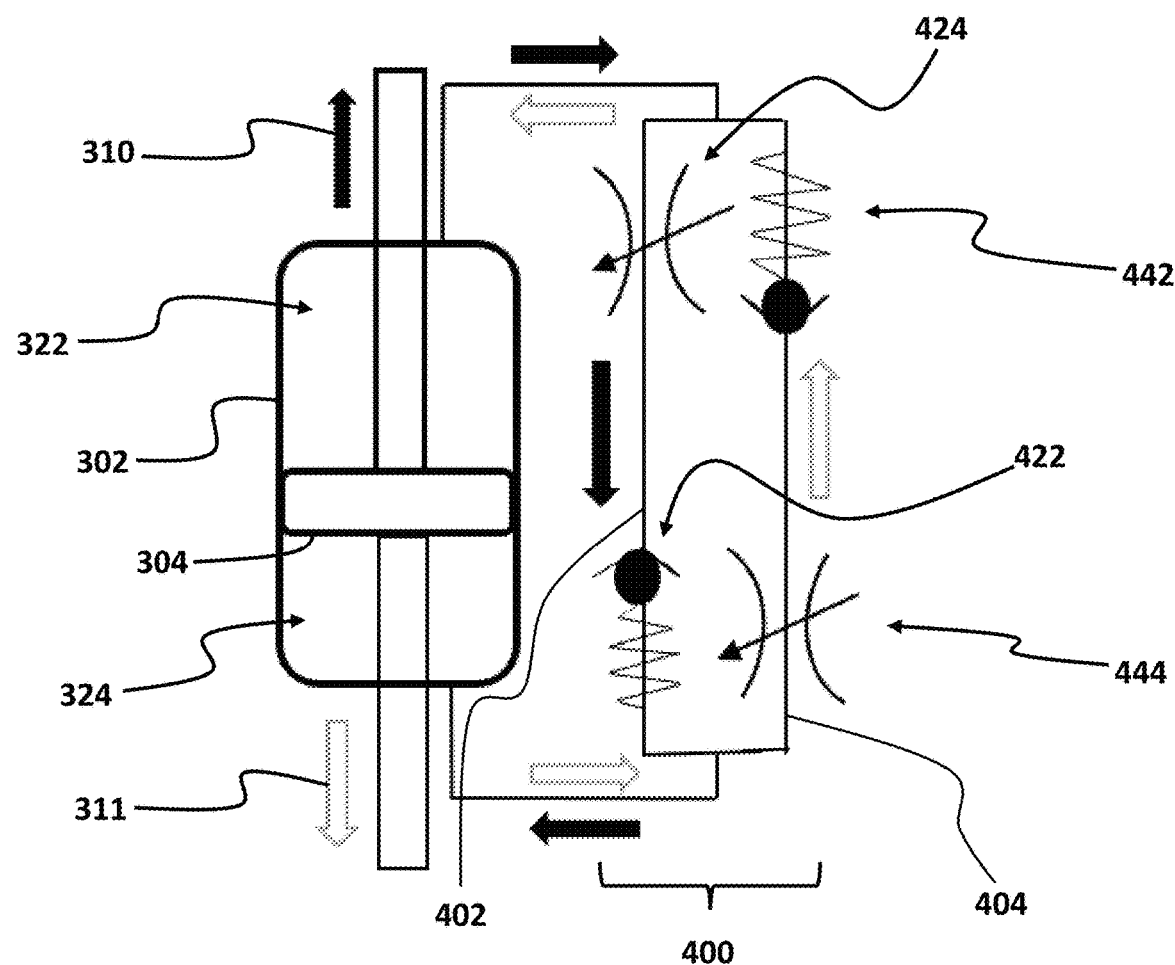
FIG. 4A illustrates a schematic of a hydraulic mechanism, consistent with one or more exemplary embodiments of the present disclosure.

FIG. 4A shows a schematic of hydraulic mechanism 105, consistent with one or more exemplary embodiments of the present disclosure. As shown in FIG. 4A, in an exemplary embodiment, hydraulic mechanism 105 may include a hydraulic circuit 400. In an exemplary embodiment, hydraulic circuit 400 may be configured to control fluid communication between top hydraulic chamber 322 and bottom hydraulic chamber 324. In an exemplary embodiment, hydraulic circuit 400 may include a first hydraulic hose 402 and a second hydraulic hose 404. In an exemplary embodiment, top hydraulic chamber 322 may be in fluid communication with bottom hydraulic chamber 324 through first hydraulic hose 402. In an exemplary embodiment, the hydraulic oil may be able to move from top hydraulic chamber 322 to bottom hydraulic chamber 324 through first hydraulic hose 402. In an exemplary embodiment, top hydraulic chamber 322 may be in fluid communication with bottom hydraulic chamber 324 through second hydraulic hose 404. In an exemplary embodiment, the hydraulic oil may flow from bottom hydraulic chamber 324 to top hydraulic chamber 322 through second hydraulic hose 404.

In an exemplary embodiment, first hydraulic hose 402 may include a first check valve 422 and a first regulating valve 424. In an exemplary embodiment, first check valve 422 may allow fluid communication from top hydraulic chamber 322 to bottom hydraulic chamber 324. In an exemplary embodiment, first check valve 422 may prevent fluid communication from bottom hydraulic chamber 324 to top hydraulic chamber 322. In an exemplary embodiment, first regulating valve 424 may be configured to control fluid flow from top hydraulic chamber 322 to bottom hydraulic chamber 324 through first hydraulic hose 402. In an exemplary embodiment, it may be understood that first regulating valve 424 may provide significant benefits including, but not limited to, provide a facility for controlling flow of the hydraulic oil from top hydraulic chamber 322 to bottom hydraulic chamber 324.

In an exemplary embodiment, second hydraulic hose 404 may include a second check valve 442 and a second regulating valve 444. In an exemplary embodiment, second check valve 442 may allow fluid communication from bottom hydraulic chamber 324 to top hydraulic chamber 322. In an exemplary embodiment, second check valve 442 may prevent fluid communication from top hydraulic chamber 322 to bottom hydraulic chamber 324. In an exemplary embodiment, second regulating valve 444 may be configured to control fluid flow from bottom hydraulic chamber 324 to top hydraulic chamber 322 through second hydraulic hose 404. In an exemplary embodiment, it may be understood that second regulating valve 444 may provide significant benefits including, but not limited to, provide a facility for controlling flow of the hydraulic oil from bottom hydraulic chamber 324 to top hydraulic chamber 322.

In an exemplary embodiment, when hydraulic piston 304 moves up in a first direction 310 and inside hydraulic cylinder 302, the hydraulic oil may flow from top hydraulic chamber 322 to bottom hydraulic chamber 324 through first hydraulic hose 402. In an exemplary embodiment, flow of the hydraulic oil may be changed by adjusting first regulating valve 424. In an exemplary embodiment, it may be understood that a speed of hydraulic piston 304 at an upward movement may be controlled by controlling flow of the hydraulic oil inside first hydraulic hose 402. In an exemplary embodiment, it may be understood that lower flow of the hydraulic oil inside first hydraulic hose 402 may lead to a lower speed of hydraulic piston 304 at an upward movement. In an exemplary embodiment, it may be understood that when first regulating valve 424 is adjusted in such a way that flow of the hydraulic oil inside first hydraulic hose 402 is relatively small, hydraulic circuit 400 may act as a damper for upward movement of hydraulic piston 304 inside hydraulic cylinder 302.

In an exemplary embodiment, when hydraulic piston 304 moves down in a second direction 311 and inside hydraulic cylinder 302, the hydraulic oil may flow from bottom hydraulic chamber 324 to top hydraulic chamber 322 through second hydraulic hose 404. In an exemplary embodiment, flow of the hydraulic oil may be changed by adjusting first regulating valve 424. In an exemplary embodiment, it may be understood that a speed of hydraulic piston 304 at a downward movement may be controlled by controlling flow of the hydraulic oil inside second hydraulic hose 404. In an exemplary embodiment, it may be understood that lower flow of the hydraulic oil inside second hydraulic hose 404 may lead to a lower speed of hydraulic piston 304 at a downward movement. In an exemplary embodiment, it may be understood that when second regulating valve 444 is adjusted in such a way that flow of the hydraulic oil inside second hydraulic hose 404 is relatively small, hydraulic circuit 400 may act as a damper for downward movement of hydraulic piston 304 inside hydraulic cylinder 302.

Figure 4B:
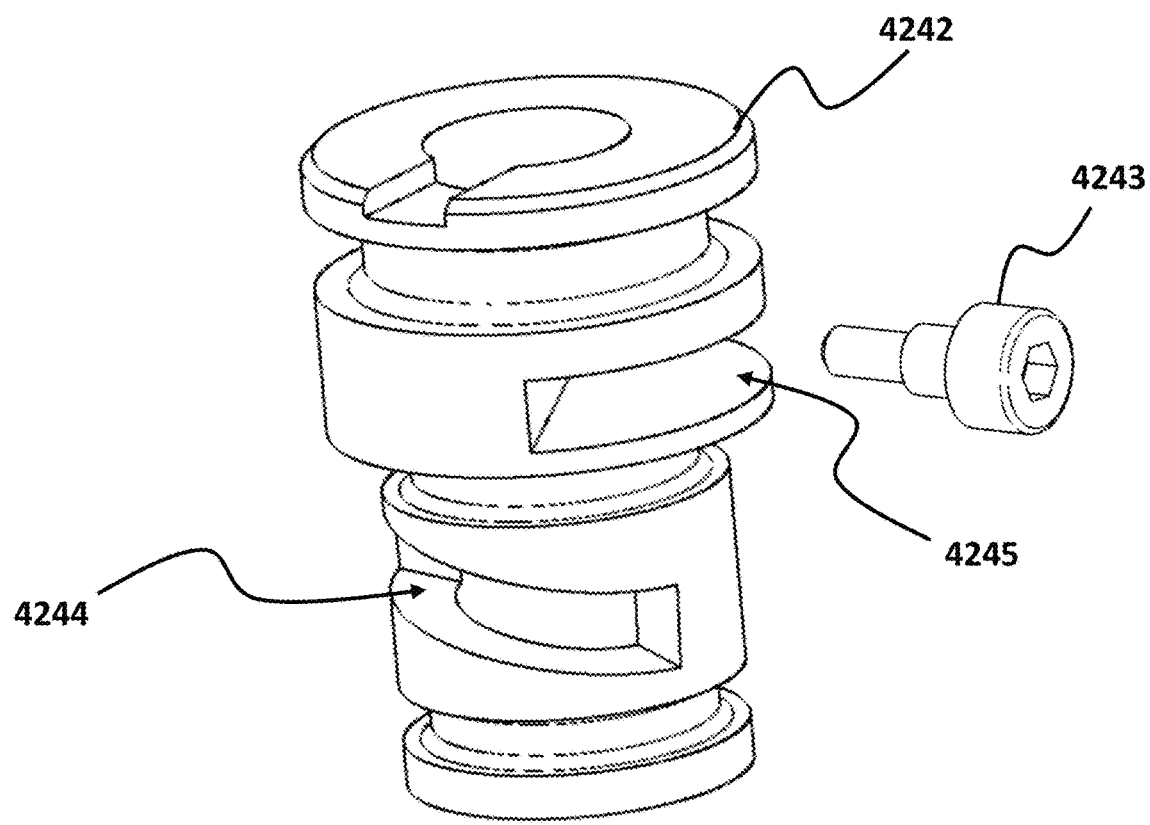
FIG. 4B illustrates a first regulating valve, consistent with one or more exemplary embodiments of the present disclosure.
Figure 4C:
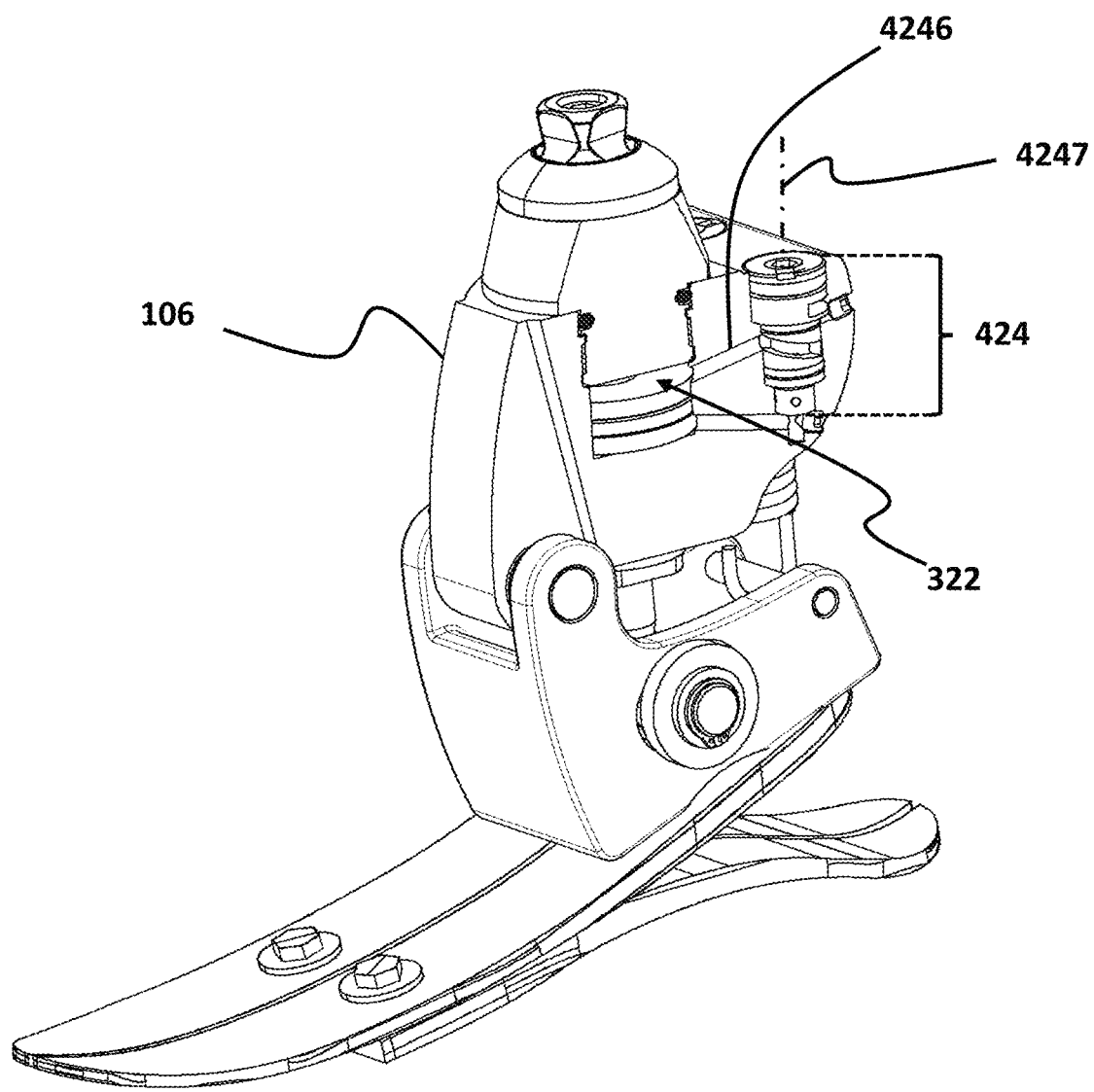
FIG. 4C illustrates a first regulating valve inside a passive ankle-foot prosthesis, consistent with one or more exemplary embodiments of the present disclosure.

FIG. 4B shows first regulating valve 424, consistent with one or more exemplary embodiments of the present disclosure. As shown in FIG. 4B, in an exemplary embodiment, first regulating valve 424 may include a first hollow cylinder 4242 and a first helical slot 4244 provided on first hollow cylinder 4242. FIG. 4C shows first regulating valve 424 inside passive ankle-foot prosthesis 100, consistent with one or more exemplary embodiments of the present disclosure. As shown in FIG. 4C, in an exemplary embodiment, first regulating valve 424 may further include a first hole 4246 provided on yoke 106. In an exemplary embodiment, first hole 4246 may be located between top hydraulic chamber 322 and first helical slot 4244. In an exemplary embodiment, first hole 4246 and first helical slot 4244 may be configured to change an area of a common section of first hole 4246 and first helical slot 4244 responsive to rotating first hollow cylinder 4242 around a first axis 4247. In an exemplary embodiment, first axis 4247 may be a main axis of first hollow cylinder 4242. In an exemplary embodiment, it may be understood that when an area of a common section of first hole 4246 and first helical slot 4244 is changed, a flow passing through first regulating valve 424 may be regulated.

In an exemplary embodiment, first regulating valve 424 may further include a lock screw 4243 and a lock slot 4245. In an exemplary embodiment, lock slot 4245 may be configured to receive lock screw 4243. In an exemplary embodiment, when lock screw 4243 is disposed inside lock slot 4245, first hollow cylinder 4242 may be limited in range of rotation around first axis 4247. In an exemplary embodiment, it may be understood that when first hollow cylinder 4242 is limited in range of rotation around first axis 4247, the area of a common section of first hole 4246 and first helical slot 4244 may not become zero. Consequently, the fluid communication between top hydraulic chamber 322 and bottom hydraulic chamber 324 may not be stopped. In an exemplary embodiment, second regulating valve 444 may be similar in structure and functionality to first regulating valve 424.

Figure 5:
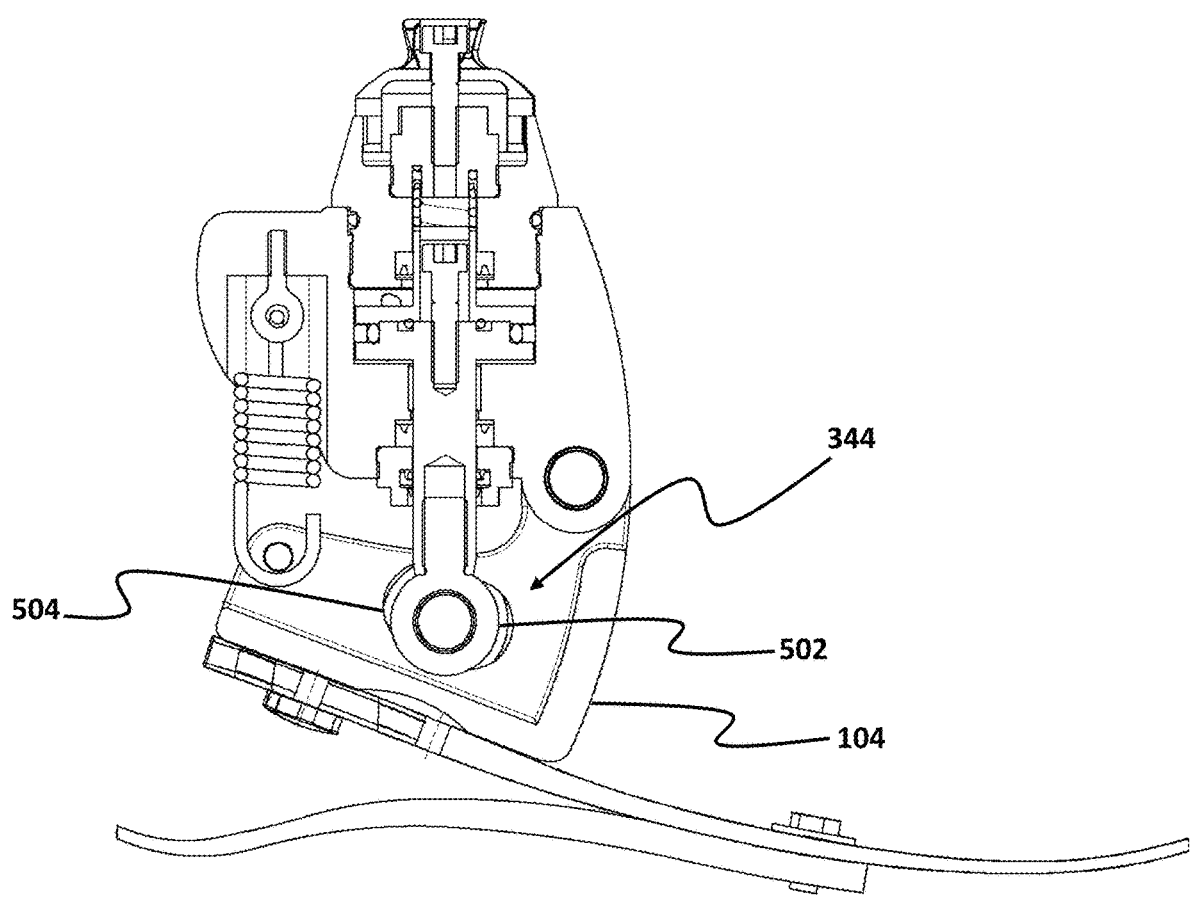
FIG. 5 illustrates a section side view of a passive ankle-foot prosthesis, consistent with one or more exemplary embodiments of the present disclosure.

FIG. 5 shows a section side view of passive ankle-foot prosthesis 100, consistent with one or more exemplary embodiments of the present disclosure. As shown in FIG. 5, in an exemplary embodiment, second end 344 of hydraulic piston 304 may include a disc slider 502 which may have a circular shape. In an exemplary embodiment, disc slider 502 may have any other geometrical shape. As further shown in FIG. 5, in an exemplary embodiment, passive ankle-foot prosthesis 100 may include a guide elongated hole 504 provided on ankle frame 104. In an exemplary embodiment, disc slider 502 may be disposed movably inside guide elongated hole 504. In an exemplary embodiment, when disc slider 502 is disposed movably inside guide elongated hole 504, disc slider 502 may be able to move inside guide elongated hole 504. In an exemplary embodiment, guide elongated hole 504 may be configured to control movements of hydraulic piston 304 inside hydraulic cylinder 302.

Figure 6:
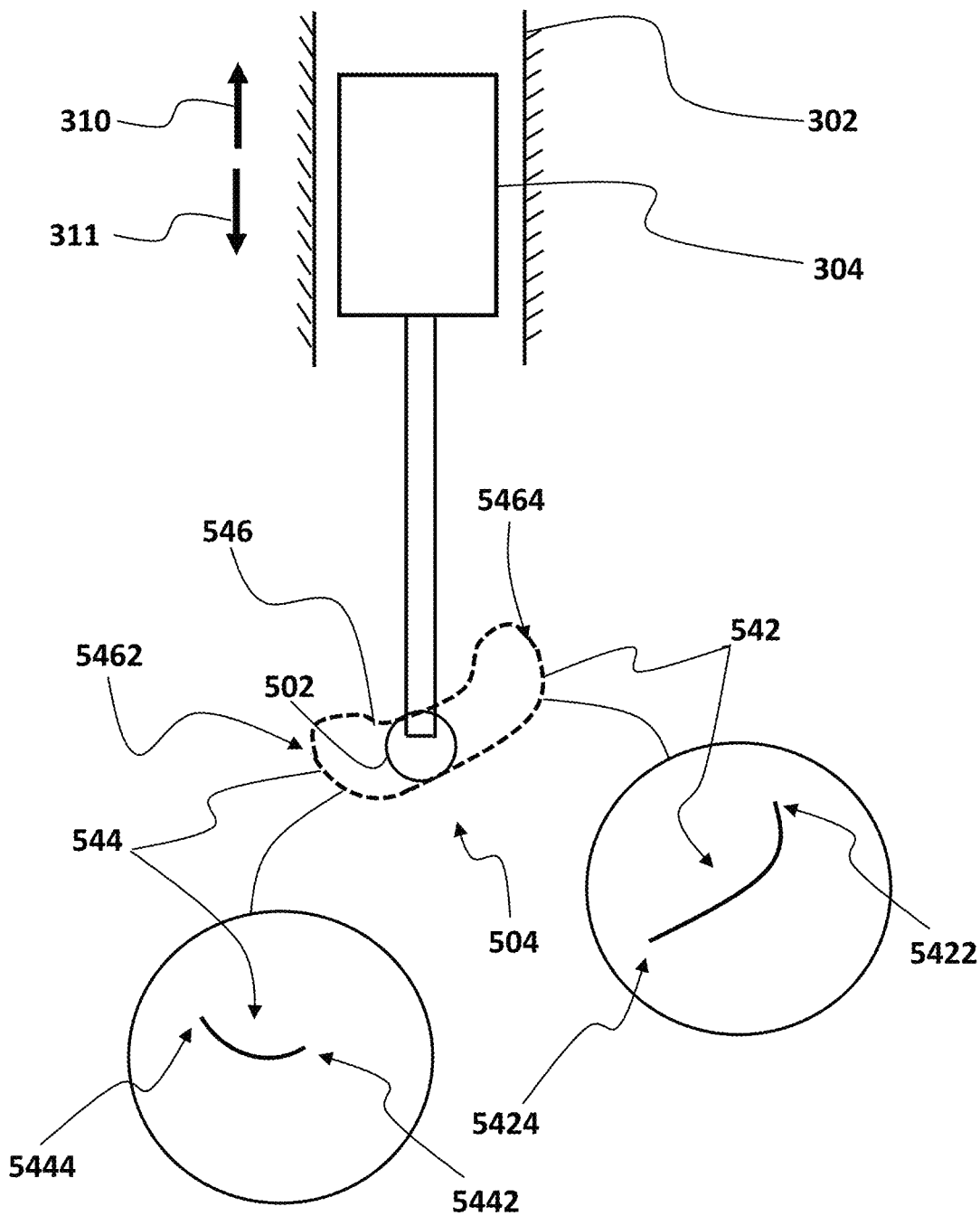
FIG. 6 illustrates a schematic of a hydraulic mechanism, consistent with one or more exemplary embodiments of the present disclosure.

FIG. 6 shows a schematic of hydraulic mechanism 105, consistent with one or more exemplary embodiments of the present disclosure. As shown in FIG. 6, in an exemplary embodiment, guide elongated hole 504 may include a first curved surface 542, a second curved surface 544, and a third curved surface 546. In an exemplary embodiment, a first end 5442 of second curved surface 544 may be connected to a second end 5424 of first curved surface 542. In an exemplary embodiment, a second end 5444 of second curved surface 544 may be connected to a first end 5462 of third curved surface 546. In an exemplary embodiment, a second end 5464 of third curved surface 546 may be connected to a first end 5422 of first curved surface 542.

In an exemplary embodiment, when yoke 106 rotates in the counter-clockwise direction between a first position and a second position, disc slider 502 may move along first curved surface 542 between second end 5424 of first curved surface 542 and first end 5422 of first curved surface 542. In an exemplary embodiment, when disc slider 502 moves along first curved surface 542 between second end 5424 of first curved surface 542 and first end 5422 of first curved surface 542, guide elongated hole 504 may urge hydraulic piston 304 to move inside hydraulic cylinder 302 and in first direction 310. In an exemplary embodiment, it may be understood that a curvature of first curved surface 542 may be designed in such a way that when disc slider 502 moves along first curved surface 542 between second end 5424 of first curved surface 542 and first end 5422 of first curved surface 542, guide elongated hole 504 urges hydraulic piston 304 to move inside hydraulic cylinder 302 and in first direction 310. In an exemplary embodiment, it may be understood that yoke 106 is in the first position when a user's gait cycle is at a first point of the user's gait cycle. In an exemplary embodiment, the first point of the user's gait cycle may also be referred to as heel contact point of the user's gait cycle. In an exemplary embodiment, the heel contact point of the user's gait cycle may refer to a point in the user's gait cycle when the user's foot initially makes contact with the ground. In an exemplary embodiment, it may be understood that yoke 106 is in the second position when a user's gait cycle is at a second point of the user's gait cycle. In an exemplary embodiment, the second point of the user's gait cycle may also be known as foot flat point of the user's gait cycle. In an exemplary embodiment, the foot flat point of the user's gait cycle may refer to a point in the user's gait cycle when the user's toe makes contact with the ground. FIG. 0.7A shows passive ankle-foot prosthesis 100 in a scenario in which a user's gait cycle is at the first point of the user's gait cycle, consistent with one or more exemplary embodiments of the present disclosure. FIG. 0.7B shows passive ankle-foot prosthesis 100 in a scenario in which a user's gait cycle is at the second point of the user's gait cycle, consistent with one or more exemplary embodiments of the present disclosure.

In an exemplary embodiment, when yoke 106 rotates in the clockwise direction between the second position and a third position, disc slider 502 may move along first curved surface 542 between first end 5422 of first curved surface 542 and second end 5424 of first curved surface 542. In an exemplary embodiment, when disc slider 502 moves along first curved surface 542 between first end 5422 of first curved surface 542 and second end 5424 of first curved surface 542, guide elongated hole 504 may urge hydraulic piston 304 to move inside hydraulic cylinder 302 and in second direction 311. In an exemplary embodiment, it may be understood that a curvature of first curved surface 542 may be designed in such a way that when disc slider 502 moves along first curved surface 542 between first end 5422 of first curved surface 542 and second end 5424 of first curved surface 542, guide elongated hole 504 urges hydraulic piston 304 to move inside hydraulic cylinder 302 and in second direction 311. In an exemplary embodiment, it may be understood that yoke 106 is in the third position when a user's gait cycle is at a third point of the user's gait cycle. In an exemplary embodiment, the third point of the user's gait cycle may also be known as mid stance point of the user's gait cycle. In an exemplary embodiment, the mid stance point of the user's gait cycle may refer to a point in user's walking at which the raised leg passes the grounded leg that is supporting the user's weight. FIG. 0.7C shows passive ankle-foot prosthesis 100 in a scenario in which a user's gait cycle is at the third point of the user's gait cycle, consistent with one or more exemplary embodiments of the present disclosure.

In an exemplary embodiment, when yoke 106 rotates in the clockwise direction between the third position and a fourth position, disc slider 502 may move along second curved surface 544 between first end 5442 of second curved surface 544 and second end 5444 of second curved surface 544. In an exemplary embodiment, when disc slider 502 moves along second curved surface 544 between first end 5442 of second curved surface 544 and second end 5444 of second curved surface 544, guide elongated hole 504 may prevent movements of hydraulic piston 304 inside hydraulic cylinder 302. In an exemplary embodiment, a length and a shape of first curved surface 542 and a length and a shape of second curved surface 544 may be configured in such a way that the range of motion may never exceed the predicted path of the second curved surface. In an exemplary embodiment, it may be understood that when guide elongated hole 504 prevents movements of hydraulic piston 304 inside hydraulic cylinder 302, hydraulic piston 304 may not move inside hydraulic cylinder 302 neither in first direction 310 or second direction 311. In an exemplary embodiment, second curve surface 544 may include an arc of a circle. In an exemplary embodiment, a center of the circle may pass through pivot axis 1422. In an exemplary embodiment, it may be understood that when second curve surface 544 includes an arc of a circle whose center passes through pivot axis 1422 and disc slider 502 moves along second curved surface 544, hydraulic piston 304 may remain immobile inside hydraulic cylinder 302. In an exemplary embodiment, when hydraulic piston 304 remains immobile inside hydraulic cylinder 302, it may mean that hydraulic piston 304 is prevented from moving up and/or down inside hydraulic cylinder 302. In an exemplary embodiment, it may be understood that yoke 106 is in the fourth position when a user's gait cycle is at a fourth point of the user's gait cycle. In an exemplary embodiment, the fourth point of the user's gait cycle may also be referred to as heel off point of the user's gait cycle. In an exemplary embodiment, the heel off point of the user's gait cycle may refer to a point in the user's gait cycle when the user's heel initially loses contact with the ground. FIG. 0.7D shows passive ankle-foot prosthesis 100 in a scenario in which a user's gait cycle is at the fourth point of the user's gait cycle, consistent with one or more exemplary embodiments of the present disclosure.

In an exemplary embodiment, when yoke 106 rotates in the counter-clockwise direction between the fourth position and a fifth position, disc slider 502 may move along second curved surface 544 between second end 5444 of second curved surface 544 and first end 5442 of second curved surface 544. In an exemplary embodiment, when disc slider 502 moves along second curved surface 544 between second end 5444 of second curved surface 544 and first end 5442 of second curved surface 544, guide elongated hole 504 may prevent movements of hydraulic piston 304 inside hydraulic cylinder 302. In an exemplary embodiment, it may be understood that when guide elongated hole 504 prevents movements of hydraulic piston 304 inside hydraulic cylinder 302, hydraulic piston 304 may not move inside hydraulic cylinder 302 neither in first direction 310 or second direction 311. In an exemplary embodiment, it may be understood that yoke 106 is in the fifth position when a user's gait cycle is at a fifth point of the user's gait cycle. In an exemplary embodiment, the fifth point of the user's gait cycle may also be known as toe off point of the user's gait cycle. In an exemplary embodiment, the toe off point of the user's gait cycle at which the user's foot rises from the ground or floor. FIG. 0.7E shows passive ankle-foot prosthesis 100 in a scenario in which a user's gait cycle is at the fifth point of the user's gait cycle, consistent with one or more exemplary embodiments of the present disclosure. FIG. 7F shows a user's gait cycle, consistent with one or more exemplary embodiments of the present disclosure. As it is shown in FIG. 7F, heel contact point of the user's gait cycle is labeled 701, foot flat point of the user's gait cycle is labeled 703, mid stance point of the user's gait cycle is labeled 705, heel off point of the user's gait cycle is labeled 707, and toe off point of the user's gait cycle is labeled 709.

Referring back to FIG. 4A, in an exemplary embodiment, first regulating valve 424 may be set in such a way that the hydraulic oil flows from top hydraulic chamber 322 to bottom hydraulic chamber 324 at a relatively high flow. In an exemplary embodiment, it may be understood that when hydraulic oil flows from top hydraulic chamber 322 to bottom hydraulic chamber 324 at a relatively high flow, hydraulic mechanism 105 may apply a relatively low resistance against hydraulic piston's 304 movement in first direction 310. In an exemplary embodiment, second regulating valve 444 may be set in such a way that the hydraulic oil flows from bottom hydraulic chamber 324 to top hydraulic chamber 322 at a relatively low flow. In an exemplary embodiment, it may be understood that when hydraulic oil flows from bottom hydraulic chamber 324 to top hydraulic chamber 322 at a relatively low flow, hydraulic mechanism 105 may apply a high resistance against hydraulic piston's 304 movement in second direction 310.

As described above, in an exemplary embodiment, when yoke 106 moves from the first position to the second position, hydraulic piston 304 may move in first direction 310 with a relatively low resistance, and consequently, hydraulic mechanism 105 may apply a low resistance against rotational movement of yoke 106. Furthermore, when yoke 106 moves from the first position to the second position, spring 108 may apply no force to yoke 106 and/or ankle frame 104.

In an exemplary embodiment, when yoke 106 moves from the second position to the third position, hydraulic piston 304 may move in second direction 311 with a relatively high resistance, and consequently, hydraulic mechanism 105 may apply a high resistance against rotational movement of yoke 106. In an exemplary embodiment, it may be understood that when hydraulic mechanism 105 applies a high resistance against rotational movement of yoke 106, hydraulic mechanism 105 may act as a damper. Furthermore, when yoke 106 moves from the second position to the third position, spring 108 may apply no force to yoke 106 and/or ankle frame 104.

In an exemplary embodiment, when yoke 106 moves from the third position to the fourth position, hydraulic piston 304 may remain immobile inside hydraulic cylinder 302, and consequently, hydraulic mechanism 105 may apply no resistance against rotational movement of yoke 106. Furthermore, when yoke 106 moves from the third position to the fourth position, spring 108 may have a length larger than a natural length of spring 108, and consequently, may apply a downward force to yoke 106 and also may apply an upward force to ankle frame 104.

In an exemplary embodiment, when yoke 106 moves from the fourth position to the fifth position, hydraulic piston 304 may remain immobile inside hydraulic cylinder 302, and consequently, hydraulic mechanism 105 may apply no resistance against rotational movement of yoke 106. Furthermore, when yoke 106 moves from the fourth position to the fifth position, spring 108 may have a length larger than a natural length of spring 108, and consequently, may apply a downward force to yoke 106 and also may apply an upward force to ankle frame 104.

Figure 7A:
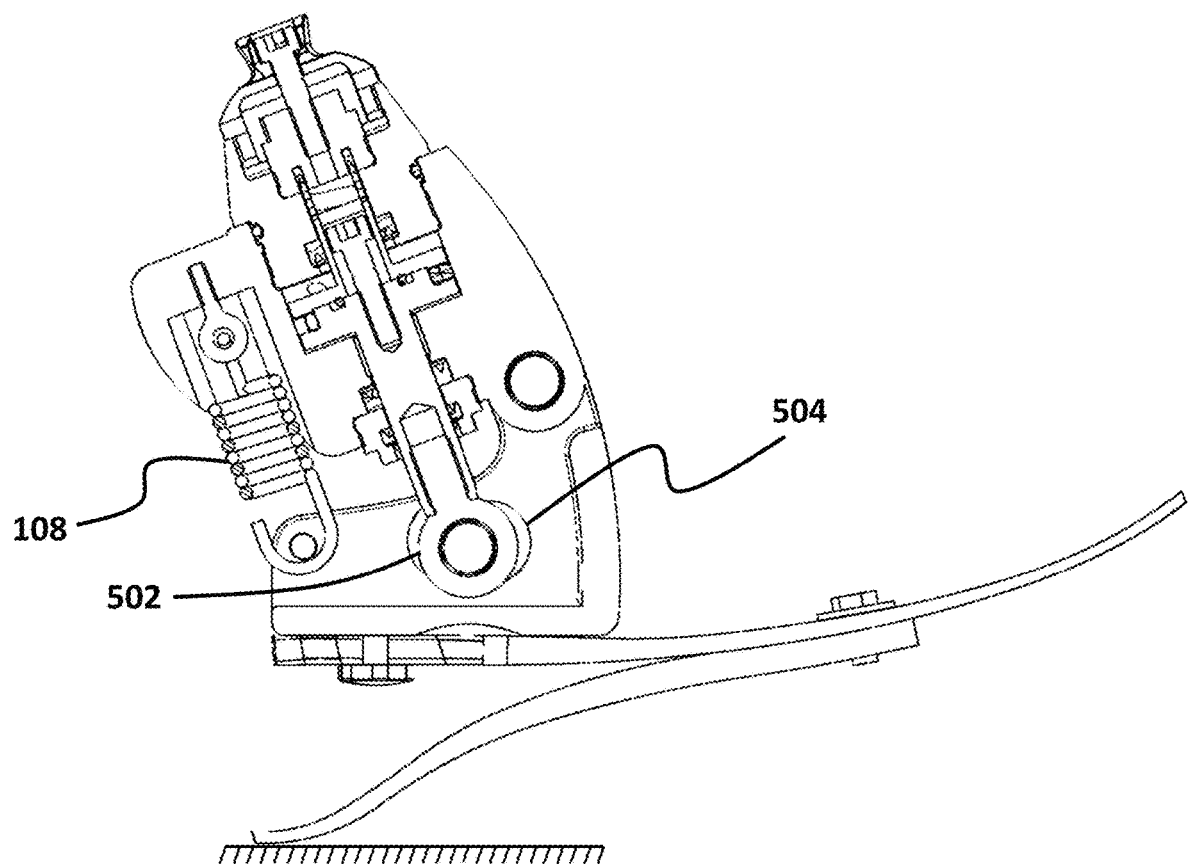
FIG. 7A illustrates a passive ankle-foot prosthesis in a scenario in which a user's gait cycle is at a first point of the user's gait cycle, consistent with one or more exemplary embodiments of the present disclosure.
Figure 7B:
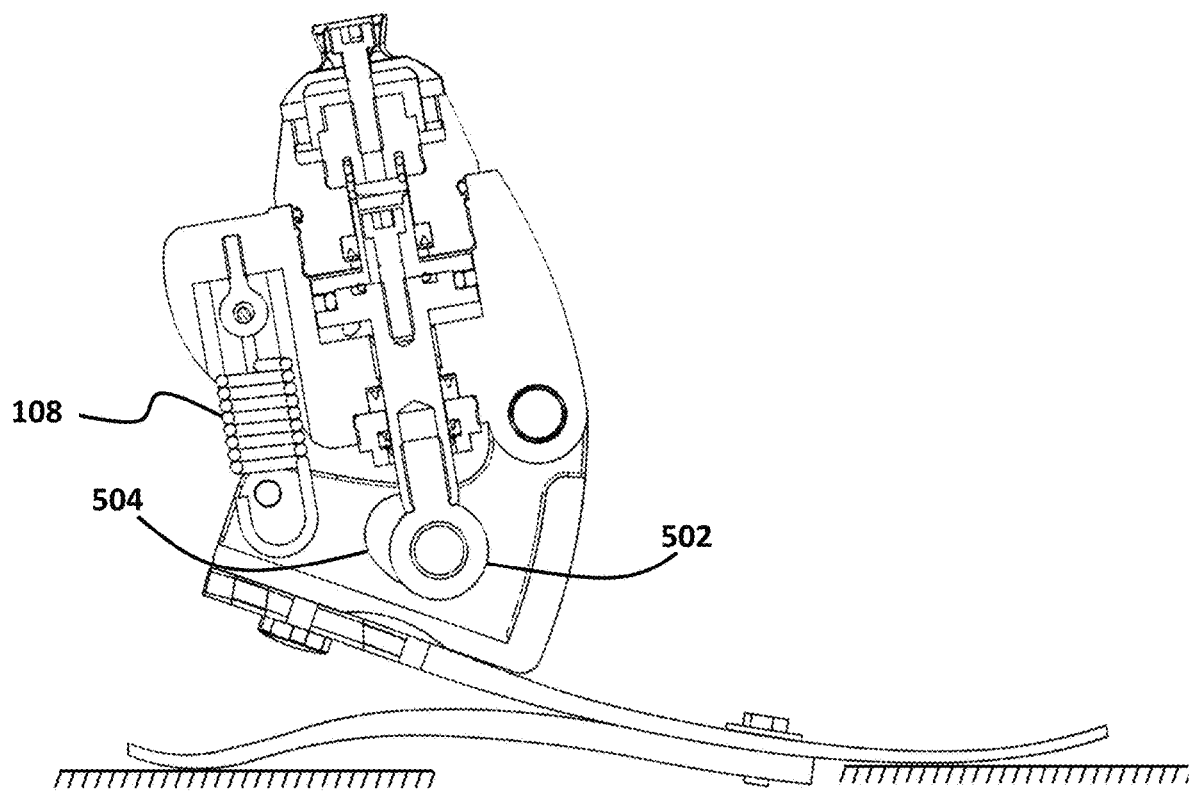
FIG. 7B illustrates a passive ankle-foot prosthesis in a scenario in which a user's gait cycle is at a second point of a user's gait cycle, consistent with one or more exemplary embodiments of the present disclosure.
Figure 7C:
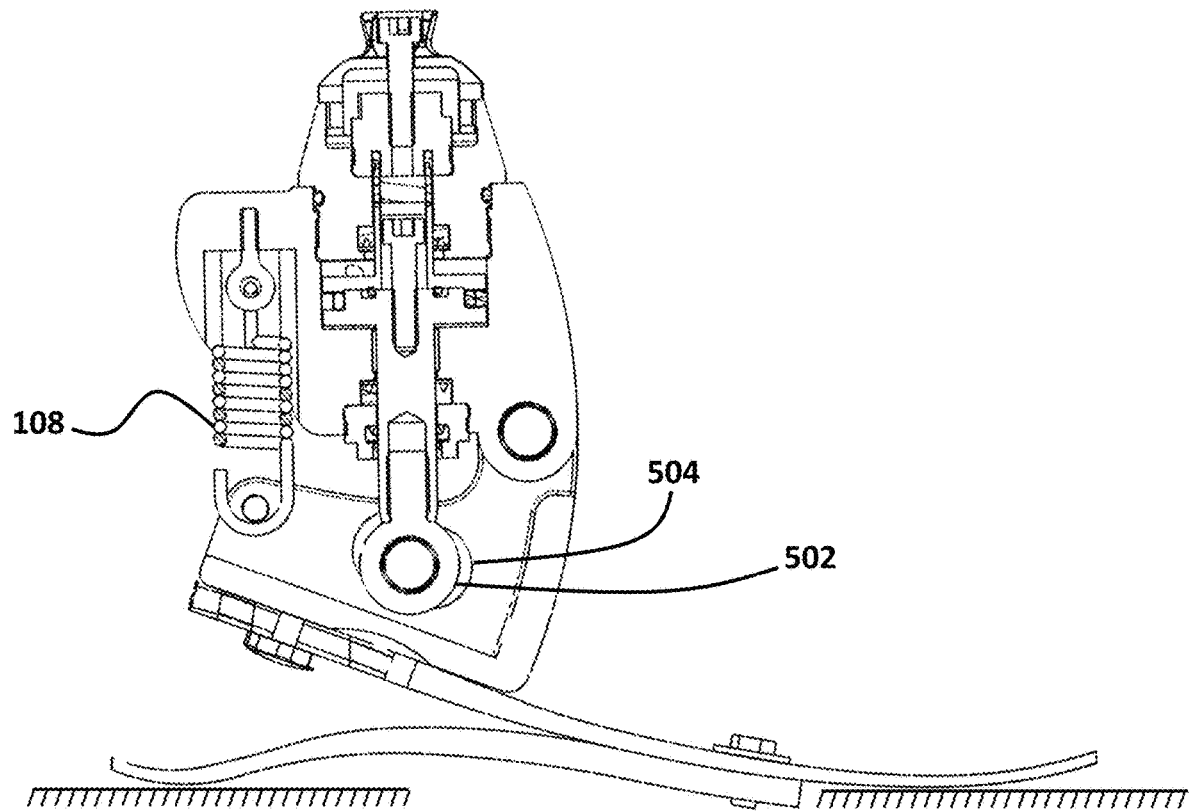
FIG. 7C illustrates a passive ankle-foot prosthesis in a scenario in which a user's gait cycle is at a third point of a user's gait cycle, consistent with one or more exemplary embodiments of the present disclosure.
Figure 7D:
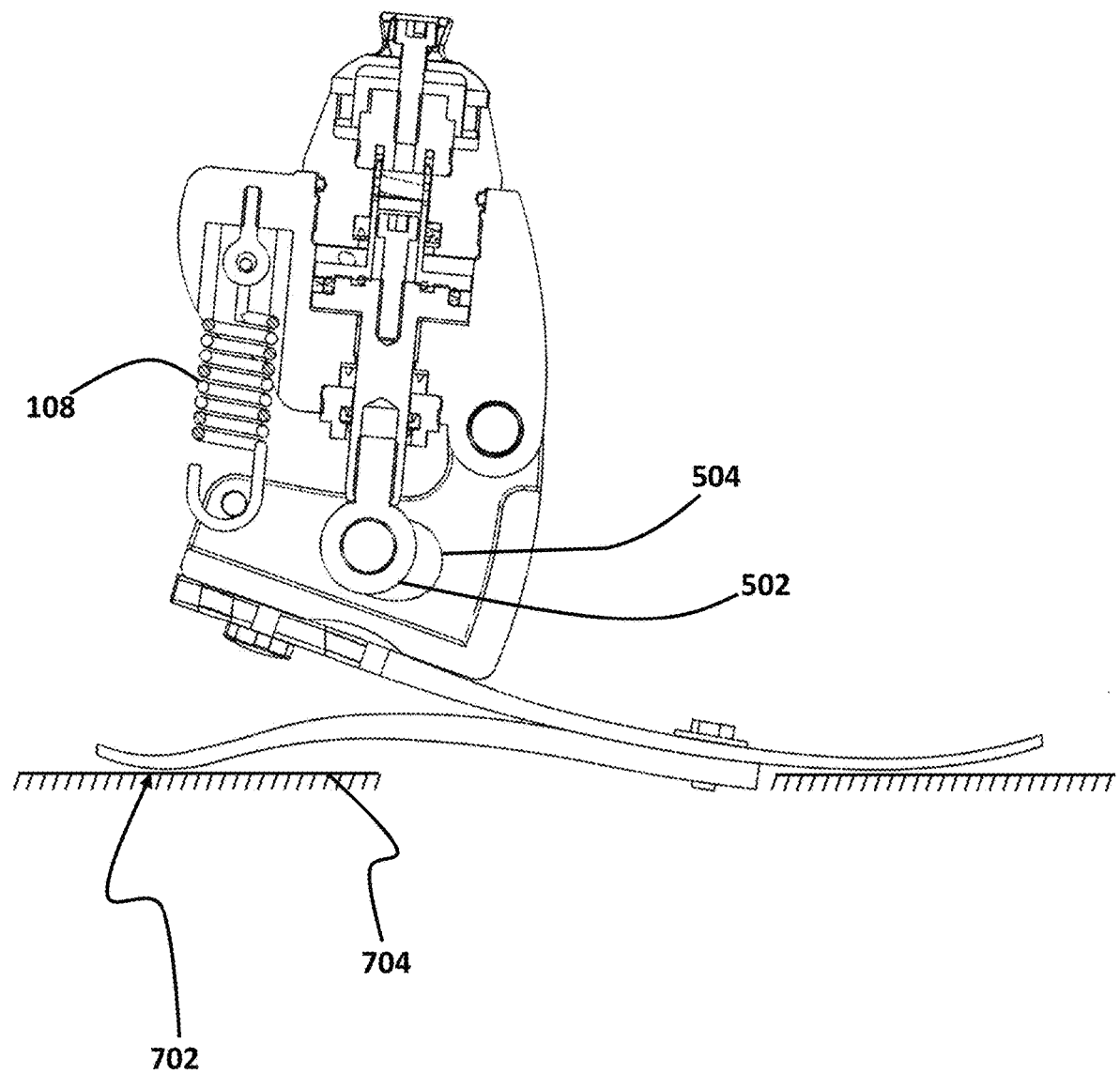
FIG. 7D illustrates a passive ankle-foot prosthesis in a scenario in which a user's gait cycle is at a fourth point of a user's gait cycle, consistent with one or more exemplary embodiments of the present disclosure.
Figure 7E:
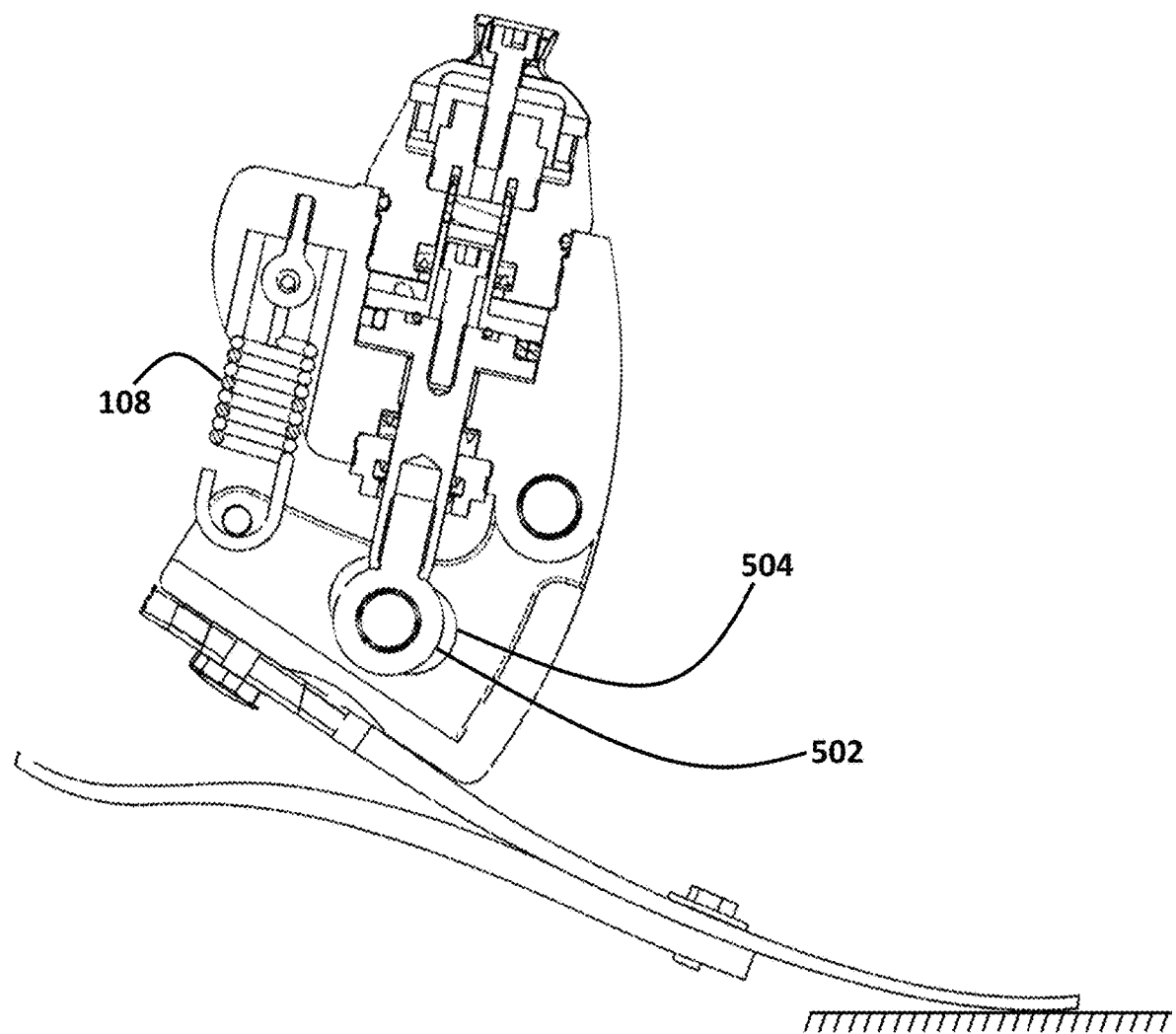
FIG. 7E illustrates a passive ankle-foot prosthesis in a scenario in which a user's gait cycle is at a fifth point of a user's gait cycle, consistent with one or more exemplary embodiments of the present disclosure.
Figure 7F:
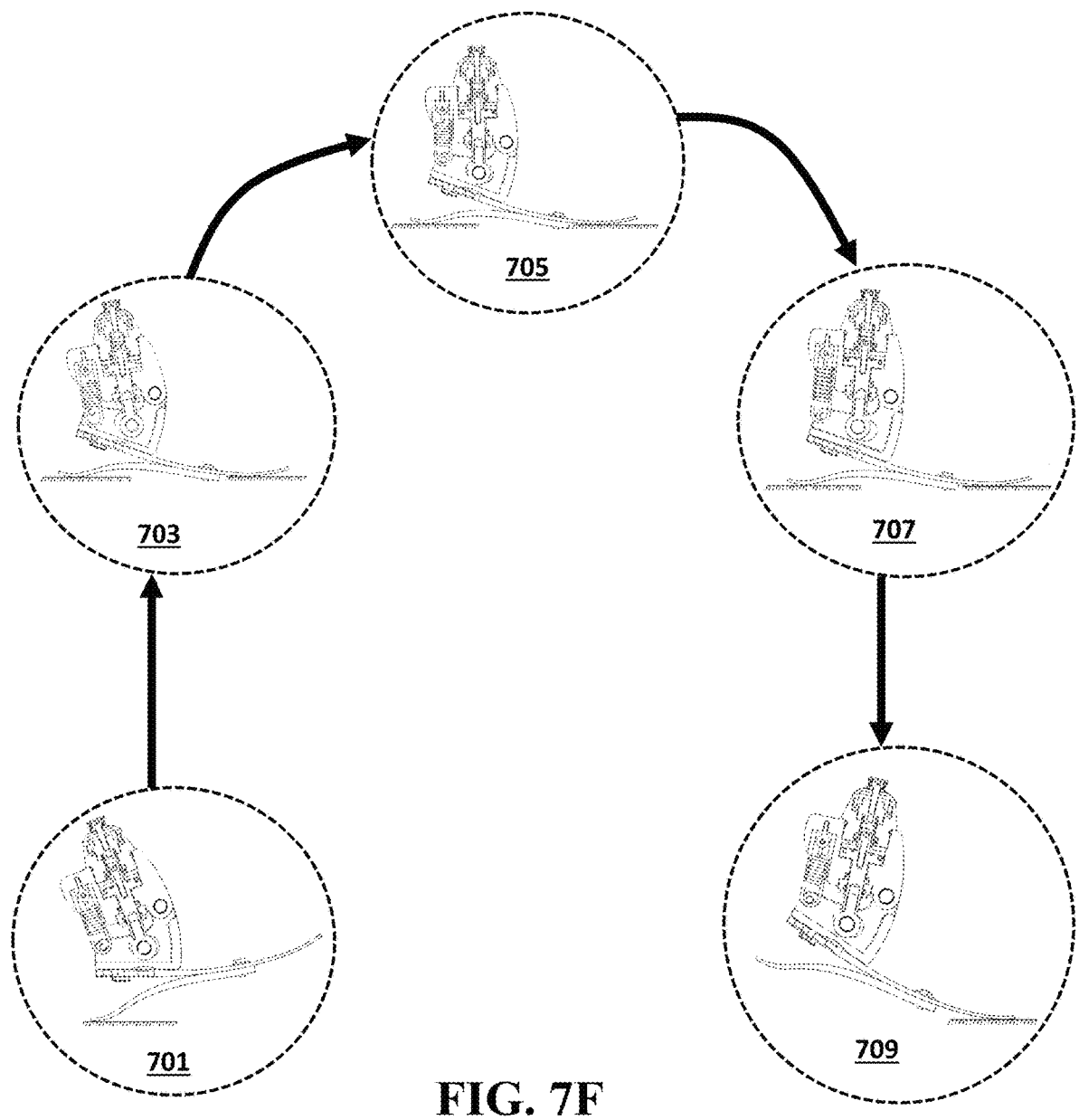
FIG. 7F illustrates a user's gait cycle, consistent with one or more exemplary embodiments of the present disclosure.

With reference to FIG. 7D, it may be understood that when yoke 106 moves from the fourth position to the fifth position, the upward force applied by spring 108 to ankle frame 104 may help a heel point 702 of foot part 102 to separate from a surface 704 more easily. In an exemplary embodiment, it may be understood that spring 108 may be inactive when yoke 106 moves from the first position to the second position. Therefore, spring 108 may be inactive in a plantarflexion motion in the user's gait cycle. Furthermore, when yoke 106 moves from the third position to the fourth position, spring 108 may be stretched and, to thereby, save energy. In an exemplary embodiment, when yoke 106 moves from the fourth position to the fifth position, spring 108 may utilize the saved energy to apply the upward force to ankle frame 104 to help a heel point 702 of foot part 102 to separate from a surface 704 more easily.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective spaces of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A passive ankle-foot prosthesis, comprising:
   a foot part comprising:
     a bottom deflectable base plate; and
     a top deflectable plate, a first end of the top deflectable plate attached to the bottom deflectable base plate, a second end of the top deflectable plate configured to deflect relative to the first end of the top deflectable plate;
   an ankle frame attached fixedly to the second end of the top deflectable plate;
   a yoke, the yoke configured to be attached to a residual limb of a user, a first end of the yoke pivotally attached to a first end of the ankle frame utilizing a pivot, the yoke configured to rotate around a pivot axis, the pivot axis passing through the pivot; and
   a spring disposed between the ankle frame and the yoke, a first end of the spring connected to a second end of the yoke, a second end of the spring connected to a second end of the ankle frame, the spring configured to apply an upward force to the second end of the ankle frame based on the yoke's rotational movements, the spring configured to stretch based on to the yoke's position;
   a hydraulic mechanism interconnected between the ankle frame and the yoke, the hydraulic mechanism configured to resist against rotational movement of the yoke around the pivot axis, the hydraulic mechanism comprising:
     a hydraulic cylinder filled with a hydraulic oil, the hydraulic cylinder fixedly attached to the yoke; and
     a hydraulic piston, a first end of the hydraulic piston disposed slidably inside the hydraulic cylinder, a second end of the hydraulic piston connected to the ankle frame, the hydraulic cylinder comprising:
       a top hydraulic chamber above the hydraulic piston; and
       a bottom hydraulic chamber under the hydraulic piston, the bottom hydraulic chamber in fluid communication with the top hydraulic chamber; and
   a guide elongated hole on the ankle frame, the second end of the hydraulic piston disposed movably inside the guide elongated hole, the guide elongated hole configured to control movements of the hydraulic piston inside the hydraulic cylinder, the guide elongated hole comprising:
a first curved surface comprising:
a flat surface, an angle between a main plane of the flat surface and a main longitudinal axis of the hydraulic piston being less than 60°; and
a circular surface attached to the flat surface; and
a second curved surface, a first end of the second curved surface connected to a second end of the first curved surface, the second curved surface comprising a circular arc element, a center of the circular arc element coinciding the pivot axis.

2. The passive ankle-foot prosthesis of claim 1, wherein the guide elongated hole further comprises:
a third curved surface, a first end of the third curved surface connected to a second end of the second curved surface, a second end of the third curved surface connected to a first end of the first curved surface;
wherein the guide elongated hole is configured to:
urge the hydraulic piston to move inside the hydraulic cylinder and in a first direction due to the second end of the hydraulic piston moving along the first curved surface from the second end of the first curved surface to the first end of the first curved surface responsive to the yoke rotating in the counter-clockwise direction from a first position to a second position, the first position associated with a first point of the user's gait cycle, the second position associated with a second point of the user's gait cycle;
urge the hydraulic piston to move inside the hydraulic cylinder and in a second direction due to the second end of the hydraulic piston moving along the first curved surface from the first end of the first curved surface to the second end of the first curved surface responsive to the yoke rotating in the clockwise direction from the second position to a third position, the third position associated with a third point of the user's gait cycle;
prevent movement of the hydraulic piston inside the hydraulic cylinder due to the second end of the hydraulic piston moving along the second curved surface from the first end of the second curved surface to the second end of the second curved surface responsive to the yoke rotating in the clockwise direction from the third position to a fourth position, the fourth position associated with a fourth point of the user's gait cycle; and
prevent movement of the hydraulic piston inside the hydraulic cylinder due to the second end of the hydraulic piston moving along the second curved surface from the second end of the second curved surface to the first end of the second curved surface responsive to the yoke rotating in the counter-clockwise direction from the fourth position to a fifth position, the fifth position associated with a fifth point of the user's gait cycle.

3. The passive ankle-foot prosthesis of claim 2, wherein the spring is configured to:
apply no force to the yoke and to the ankle frame due to the spring being disengaged from the ankle frame responsive to the yoke rotating in the counter-clockwise direction from the first position to the second position;
apply no force to the yoke and to the ankle frame due to the spring being disengaged from the ankle frame responsive to the yoke rotating in the clockwise direction from the second position to the third position;
stretch responsive to the yoke rotating in the clockwise direction from the third position to the fourth position;
apply an upward force to the ankle frame and apply a downward force to the yoke due to the spring being stretched responsive to the yoke rotating in the counter-clockwise direction from the fourth position to the fifth position.

4. The passive ankle-foot prosthesis of claim 3, wherein the hydraulic mechanism further comprises a hydraulic circuit configured to control fluid communication between the top hydraulic chamber and the bottom hydraulic chamber, the hydraulic circuit comprising:
a first hydraulic hose with a first check valve and a first regulating valve, the top hydraulic chamber and the bottom hydraulic chamber in fluid communication through the first hydraulic hose, wherein:
the first check valve is configured to:
allow fluid communication from the top hydraulic chamber to the bottom hydraulic chamber through the first hydraulic hose; and
prevent fluid communication from the bottom hydraulic chamber to the top hydraulic chamber through the first hydraulic hose; and
the first regulating valve is configured to control fluid flow from the top hydraulic chamber to the bottom hydraulic chamber through the first hydraulic hose; and
a second hydraulic hose with a second check valve and a second regulating valve, the top hydraulic chamber and the bottom hydraulic chamber in fluid communication through the second hydraulic hose, wherein:
the second check valve is configured to:
allow fluid communication from the bottom hydraulic chamber to the top hydraulic chamber through the second hydraulic hose; and
prevent fluid communication from the top hydraulic chamber to the bottom hydraulic chamber through the second hydraulic hose; and
the second regulating valve is configured to control fluid flow from the bottom hydraulic chamber to the top hydraulic chamber.

5. The passive ankle-foot prosthesis of claim 4, wherein a value of the spring constant is in a range between 35 N/mm$^2$ and 50 N/mm$^2$.

6. The passive ankle-foot prosthesis of claim 5, wherein the hydraulic piston comprises a disc slider at the second end of the hydraulic piston, the disc slider disposed movably inside the guide elongated hole.

7. The passive ankle-foot prosthesis of claim 6, wherein the disc slider comprises a disc shape.

8. The passive ankle-foot prosthesis of claim 7, wherein the spring comprises a hook at the second end of the spring, the hook engaged with the second end of the ankle frame, the hook configured to:
allow the spring to apply an upward force to the second end of the ankle frame; and
prevent the spring to apply a downward force to the second end of the ankle frame.

9. The passive ankle-foot prosthesis of claim 8, wherein the first regulating valve comprises:
a first hollow cylinder;
a first helical slot provided on the first hollow cylinder; and
a first hole provided on the yoke between the top hydraulic chamber and the first helical slot, the first hole and the first helical slot configured to change an area of a common section of the first hole and the first helical slot responsive to rotating the first hollow cylinder around a first axis, the first axis associated with a main axis of the first hollow cylinder.

10. The passive ankle-foot prosthesis of claim 9, wherein the second regulating valve comprises:
- a second hollow cylinder;
- a second helical slot provided on the second hollow cylinder; and
- a second hole provided on the yoke between the top hydraulic chamber and the second helical slot, the second hole and the second helical slot configured to change an area of a common section of the second hole and the second helical slot responsive to rotating the second hollow cylinder around a second axis, the second axis associated with a main axis of the second hollow cylinder.

11. A passive ankle-foot prosthesis, comprising:
- a foot part comprising:
  - a bottom deflectable base plate; and
  - a top deflectable plate, a first end of the top deflectable plate attached to the bottom deflectable base plate, a second end of the top deflectable plate configured to deflect relative to the first end of the top deflectable plate;
- an ankle frame attached fixedly to the second end of the top deflectable plate;
- a yoke, the yoke configured to be attached to a residual limb of a user, a first end of the yoke pivotally attached to a first end of the ankle frame utilizing a pivot, the yoke configured to rotate around a pivot axis, the pivot axis passing through the pivot; and
- a spring disposed between the ankle frame and the yoke, a first end of the spring connected to a second end of the yoke, a second end of the spring connected to a second end of the ankle frame, the spring configured to apply an upward force to the second end of the ankle frame based on the yoke's rotational movements, the spring configured to stretch based on to the yoke's position;
- a hydraulic mechanism interconnected between the ankle frame and the yoke, the hydraulic mechanism configured to resist against rotational movement of the yoke around the pivot axis, the hydraulic mechanism comprising:
  - a hydraulic cylinder filled with a hydraulic oil, the hydraulic cylinder fixedly attached to the yoke; and
  - a hydraulic piston, a first end of the hydraulic piston disposed slidably inside the hydraulic cylinder, a second end of the hydraulic piston connected to the ankle frame, the hydraulic cylinder comprising:
    - a top hydraulic chamber above the hydraulic piston; and
    - a bottom hydraulic chamber under the hydraulic piston, the bottom hydraulic chamber in fluid communication with the top hydraulic chamber; and
- a guide elongated hole on the ankle frame, the second end of the hydraulic piston disposed movably inside the guide elongated hole, the guide elongated hole configured to control movements of the hydraulic piston inside the hydraulic cylinder, the guide elongated hole comprising an opening, the opening comprising:
  - a middle portion with two opposing surfaces parallel to each other in a longitudinal direction coinciding with a longest length of the elongated hole;
  - a left portion and a right portion both connected to the middle portion at opposite ends, respective top parts of the right portion and the left portion extending further than a top surface of the two opposing surfaces in a latitudinal directional, and respective lower parts of the right portion and left portion not extending further than a bottom surface of the two surfaces in a latitudinal direction, the longitudinal direction perpendicular to the latitudinal direction, and
  - the left portion and the right portion comprising curved surfaces.

\* \* \* \* \*